United States Patent
Fredriksson et al.

(10) Patent No.: US 12,416,040 B2
(45) Date of Patent: Sep. 16, 2025

(54) SPATIAL MAPPING BY SERIAL PRIMER EXTENSION

(71) Applicant: PIXELGEN TECHNOLOGIES AB, Stockholm (SE)

(72) Inventors: Simon Fredriksson, Bromma (SE); Filip Karlsson, Solna (SE)

(73) Assignee: PIXELGEN TECHNOLOGIES AB, Stockholm (SE)

(*) Notice: Subject to any disclaimer, the term of this patent is extended or adjusted under 35 U.S.C. 154(b) by 0 days.

(21) Appl. No.: 18/888,001

(22) Filed: Sep. 17, 2024

(65) Prior Publication Data

US 2025/0011846 A1  Jan. 9, 2025

Related U.S. Application Data

(63) Continuation of application No. 18/283,172, filed as application No. PCT/IB2022/052862 on Mar. 29, 2022, now Pat. No. 12,123,050.

(Continued)

(51) Int. Cl.
*C12Q 1/6837* (2018.01)
*C12Q 1/6841* (2018.01)

(52) U.S. Cl.
CPC ......... *C12Q 1/6837* (2013.01); *C12Q 1/6841* (2013.01)

(58) Field of Classification Search
CPC .................. C12Q 1/6837; C12Q 1/6841
See application file for complete search history.

(56) References Cited

U.S. PATENT DOCUMENTS

| | | | |
|---|---|---|---|
| 2010/0240101 A1 | 9/2010 | Lieberman et al. | |
| 2015/0044674 A1* | 2/2015 | Fredriksson | C12Q 1/6804 435/6.11 |

(Continued)

FOREIGN PATENT DOCUMENTS

| | | |
|---|---|---|
| JP | 2007525174 A | 9/2007 |
| JP | 2022513561 A | 2/2022 |

(Continued)

OTHER PUBLICATIONS

Wu et al., "Profiling surface proteins on individual exosomes using a proximity barcoding assay", Nature Communications, 2019, 10:3854, pp. 1-10.

(Continued)

*Primary Examiner* — Gary Benzion
*Assistant Examiner* — Lisa Horth
(74) *Attorney, Agent, or Firm* — James S. Keddie; Bozicevic, Field & Francis LLP

(57) ABSTRACT

Provided herein is probe system comprising: a population of nucleic acid molecules that have an extendible end, a first set of barcoded particles that each have a nucleotide sequence comprising: (i) a binding sequence that is complementary to the extendible end of the nucleic acid molecules, (ii) a unique particle identifier sequence, and (iii) a first template sequence, and a second set of barcoded particles that each have a nucleotide sequence comprising: (i) the first template sequence and (ii) a unique particle identifier sequence. In use, extension of the nucleic acid molecules using the first set of barcoded particles of as a template produces extensions products that contain the complement of a unique particle identifier sequence of a particle and the complement of the first template sequence. Methods of using the probe system to map binding events in or on a cellular sample are also provided.

12 Claims, 21 Drawing Sheets

Specification includes a Sequence Listing.

Related U.S. Application Data

(60) Provisional application No. 63/168,132, filed on Mar. 30, 2021.

(56) References Cited

U.S. PATENT DOCUMENTS

| | | |
|---|---|---|
| 2015/0298091 A1 | 10/2015 | Weitz et al. |
| 2016/0265046 A1 | 9/2016 | Zhang et al. |
| 2016/0281134 A1 | 9/2016 | Wu |
| 2021/0095331 A1* | 4/2021 | Fan .................. G01N 35/1072 |

FOREIGN PATENT DOCUMENTS

| | | | |
|---|---|---|---|
| JP | 2022554421 | A | 12/2022 |
| WO | WO 2012/057689 | A1 | 5/2012 |
| WO | WO 2012/106385 | A2 | 8/2012 |
| WO | WO 2012/112804 | A1 | 8/2012 |
| WO | WO 2015/047186 | A1 | 4/2015 |
| WO | WO 2015/058052 | A1 | 4/2015 |
| WO | WO 2016/123419 | A1 | 8/2016 |
| WO | WO 2017/044893 | A1 | 3/2017 |
| WO | WO 2017/222453 | A1 | 12/2017 |
| WO | WO 2019/099751 | A1 | 5/2019 |
| WO | WO 2019/099751 | A9 | 5/2019 |
| WO | WO 2021/084419 | A1 | 5/2021 |

OTHER PUBLICATIONS

Han, "Envisioning DNA as Photons, Broad Team Turns Sequencers Into Microscopes", GenomeWeb, Jun. 20, 2019.

Han, "SciLifeLab, Broad Institute Researchers Go High Definition With Spatial Transcriptomics", GenomeWeb, Sep. 12, 2019.

Hoffecker et al., "A computational framework for DNA sequencing microscopy", PNAS, Sep. 2019, 116(39):19282-19287.

Stuart et al., "Integrative single-cell analysis", Nature Reviews Genetics, Jan. 2019, 20: 257-272.

Weinstein et al., "DNA Microscopy: Optics-free Spatio-genetic Imaging by a Stand-Alone Chemical Reaction", Cell, Jun. 2019, 178: 1-13.

Ke et al., "In situ sequencing for RNA analysis in preserved tissue and cells", Nature Methods, 2013, 10(9):857-860.

Wu et al., "Profiling surface proteins on individual exosomes using a proximity barcoding assay" (Supplementary information), Nature Communications, Aug. 2019, 10: 3854, 12 pages.

Hoffecker et al., "A Computational Framework for DNA Sequencing-Based Microscopy", bioRxiv, Nov. 21, 2018.

Greenwood et al., "Proximity assays for sensitive quantification of proteins", Biomolecular Detection and Quantification, 2015, 4: 10-16.

* cited by examiner

- Array pixilation:
  - Immobiized primers hybridize to pixel.
  - Polymerase extension of oligos immobilized to array to incorporate 2 UMIs (sequentially).
- Sample is contacted with pixelated array. 3' ends have p(T)VN which prime cDNA synthesis of mRNA.
- 3' PCR primer is added using standard methods (template switching etc.)

1) Hybridization of Uracil pixels with hairpins

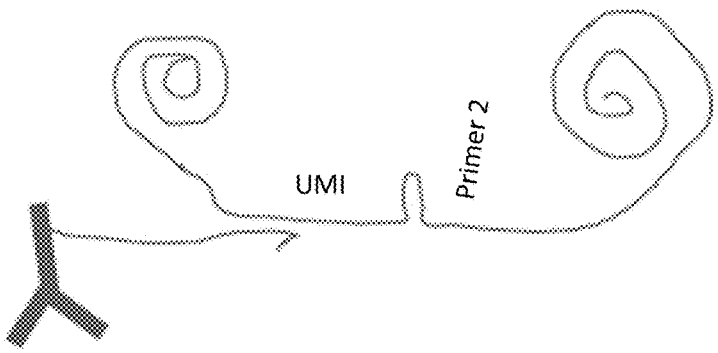

2) Extension using strand displacing DNA polymerase and dNTPs

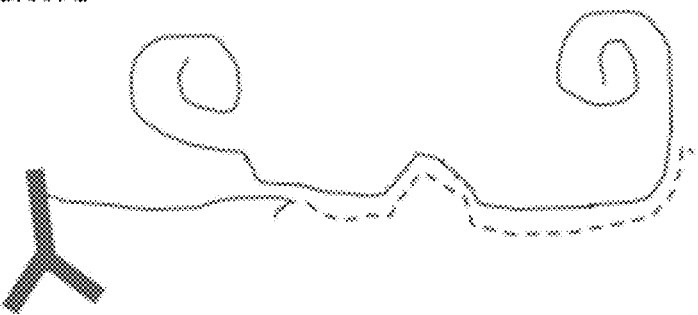

3) Uracil DNA glycosylase mediated degradation of Uracil pixels, reshapes the hairpin complement in the extension product, possibly in several copies

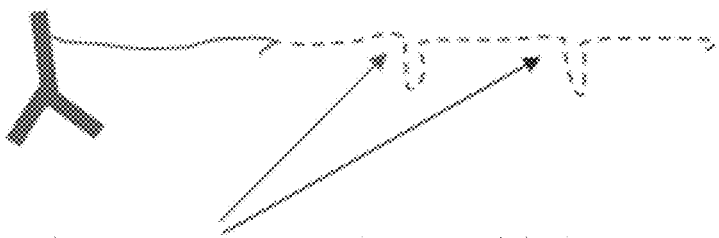

4) Restriction enzyme cleavage of the hairpin gives a new free 3'-end to be extended on the Second Uracil DNA pixel ("Primer 2"). Second pixel extension is also done with hairpin Pixels

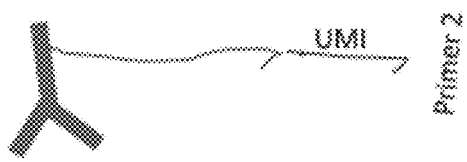

FIG. 17

SPATIAL MAPPING BY SERIAL PRIMER EXTENSION

CROSS-REFERENCING

This application is a continuation of U.S. application Ser. No. 18/283,172, filed on Sep. 20, 2023, which is a § 371 national phase of International Application No. PCT/IB2022/052862, filed on Mar. 29, 2022, which claims the benefit of U.S. provisional application Ser. no. 63/168,132, filed on Mar. 30, 2021, which applications are incorporated by reference herein in their entireties.

INCORPORATION BY REFERENCE OF SEQUENCE LISTING PROVIDED AS A SEQUENCE LISTING XML FILE

A Sequence Listing is provided herewith as a Sequence Listing XML, "PIXL-006CON_SEQLIST.xml", created on Sep. 16, 2024, and having a size of 52,979 bytes.

The contents of the Sequence Listing XML are incorporated herein by reference in their entirety.

BACKGROUND

Sample and molecule indices are commonly employed in many of today's genomics workflows. Sample indexing is a commonly used approach that enables samples to be sequenced and analyzed in a multiplex way. In sample indexing methods, all nucleic acids in a particular sample are labeled with the same sequence tag, and the tagged library is pooled with other libraries that are tagged with different barcodes, and the pool is sequenced in parallel in a single sequencing run. Then, during analysis, the sample-specific indexes allow software to separate the multiplexed sequence data into sample-specific data sets. The goal of molecular indexing, on the other hand, is to tag each molecule in a sample a unique sequence before PCR amplification. In these methods, each nucleic acid in the starting sample is tagged with a unique molecule index, and the sequence analysis software filters out duplicate reads (i.e., reads from copes of the same molecule) and eliminate PCR/sequencing errors using the index.

This disclosure employs indices to provide spatial information, which is believed to be a new use for molecular indices.

SUMMARY

This disclosure provides, among other things, a probe system comprising: (a) a population of nucleic acid molecules that have an extendible end; (b) a first set of barcoded particles that each have a nucleotide sequence comprising: (i) a binding sequence that is complementary to the extendible end of the nucleic acid molecules of (a), (ii) a unique particle identifier sequence, and (iii) a first template sequence; (c) a second set of barcoded particles that each have a nucleotide sequence comprising: (i) the first template sequence, and (ii) a unique particle identifier sequence. In this probe system, extension of the nucleic acid molecules of (a) using the first set of barcoded particles of (b) as a template produces extensions products that contain the complement of a unique particle identifier sequence of a particle of (a) (ii) and the complement of the first template sequence.

In the description that follows below, the nucleic acid molecules that have an extendible end are primers, and the method is implemented using primer extension. In alternate embodiments (illustrated in FIGS. 12-14) the method may be implemented using gap-fill/ligation or ligation-based method. As such, the present system and method should not be limited to primer extension-based methods only.

In some embodiments, the method comprises: hybridizing the first set of barcoded particles with the first population of primer molecules extending the hybridized primer molecules using the nucleotide sequence of the first set of barcoded particles as a template to produce first primer extension products that contain the complement of a unique particle identifier sequence from a barcoded particle in the first set of barcoded particles and the complement of the first template sequence; removing the first set of barcoded particles; hybridizing the first primer extension products with the second set of barcoded particles, wherein the complement of the first template sequence in the first primer extension products hybridizes to the first template sequence in the second set of barcoded particles; and extending the first primer extension products using the nucleotide sequence of the second set of barcoded particles as a template to produce second primer extension products that contain: a unique particle identifier sequence from a barcoded particle in the first set of barcoded particles, the first template sequence, and a unique particle identifier sequence from a barcoded particle in the second set of barcoded particles.

The probe system may be employed in a method of making a map of binding events on a cellular sample. In the embodiments, this method may comprise: (a) obtaining: i. a sample containing primer molecules that are bound to sites in or on cells; ii. a first set of barcoded particles that each have a nucleotide sequence comprising: (i) a primer binding sequence that is complementary to the 3' end of the primer molecules, (ii) a unique particle identifier sequence, and (iii) a first template sequence; iii. a second set of barcoded particles that each have a nucleotide sequence comprising: (i) the first template sequence, and (ii) a unique particle identifier sequence; (b) specifically hybridizing the first set of barcoded particles with the sample, wherein the nucleotide sequence of at least some of the first set of barcoded particles hybridizes to at least two primer molecules; (c) extending the primers that are hybridized to barcoded particles in step (b) using the nucleotide sequences to which the primers are hybridized as a template to produce first primer extension products that each comprise a first unique particle identifier sequence; (d) removing the first set of barcoded particles from the sample; (e) specifically hybridizing the second set of barcoded particles with the first primer extension products of (c), wherein the nucleotide sequences of at least some of the second set of barcoded particles hybridizes to at least two molecules of the primer extension products; (f) extending the first primer extension products that are hybridized to a barcoded particle in step (e) using the nucleotide sequences to which the primers are hybridized to as a template to produce second primer extension products that comprise the two unique particle identifier sequences; (g) determining which unique particle identifier sequence or complements thereof are in second primer extension products; and (h) making a map of the relative positions of the primers using the unique particle identifier sequences that is in the second primer extension products.

Alternative embodiments involve a probe system comprising: (a) a population of primer molecules; (b) a set of barcoded particles that each have a nucleotide sequence comprising: (i) a primer binding sequence that is complementary to the 3' end of the primer molecules of (a), (ii) a unique particle identifier sequence, and (iii) a first template sequence; and (c) a ligation splint comprising a first oligonucleotide and a second oligonucleotide, wherein the first oligonucleotide comprises a first sequence and the first template sequence; and the second oligonucleotide comprises a second sequence that is complementary to the first sequence, and the first template sequence.

The alternative probe system may be used in a method that comprises: i. hybridizing the set of barcoded particles of (b) with the population of primer molecules of (a), ii. extending the hybridized primer molecules using the nucleotide sequences as a template to produce first primer extension products that contain i. the complement of a unique particle identifier sequence from a barcoded particle and ii. the complement of the first template sequence; iii. removing the barcoded particles; iv. hybridizing the first primer extension products with the ligation splint, wherein the complements of the first template sequence in two proximal first primer extension products hybridize to the first and second sequences of the ligation splint; and ligating at least one of the first or the second oligonucleotide of the hybridized ligation splint to the first primer extension products and extending the 3' end of the ligated first or second oligonucleotide in the splint using the first primer extension product in the ligation product as a template, thereby adding two unique particle identifier sequences to a primer.

BRIEF DESCRIPTION OF THE FIGURES

The skilled artisan will understand that the drawings, described below, are for illustration purposes only. The drawings are not intended to limit the scope of the present teachings in any way.

FIG. 17 schematically illustrates an alternative example of how the assay can be designed so that the primer extension product end at a defined nucleotide, thereby allowing it to be used as a primer in the next step of the method.

DEFINITIONS

Figure 1:
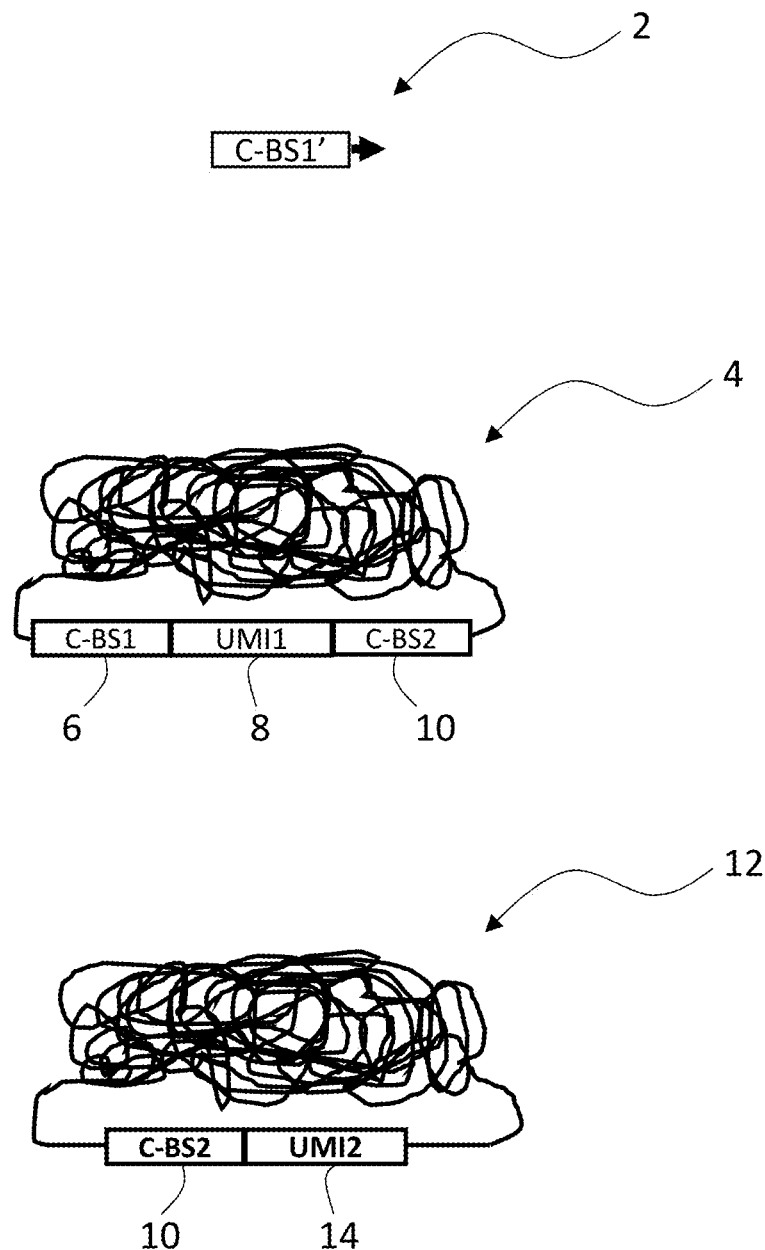
FIG. 1 schematically illustrates a probe system of the present disclosure.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; and, amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N. Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA, various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotides of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers. An oligonucleotide may be 10 to 20, 21 to 30, 31 to 40, 41 to 50, 51to 60, 61 to 70, 71 to 80, 80 to 100, 100 to 150 or 150 to 200 nucleotides in length, for example.

The term "primer" as used herein refers to an oligonucleotide that is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be single-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence or fragment, the oligonucleotide primer typically contains 15-25 or more nucleotides, although it may contain fewer nucleotides. The primers herein are selected to be substantially complementary to different strands of a particular target DNA sequence. This means that the primers must be sufficiently complementary to hybridize with their respective strands. Therefore, the primer sequence need not reflect the exact sequence of the template. For example, a non-complementary nucleotide fragments may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

The term "primer extension products" refer to the product of extension of a primer or the product of extension of a molecule that is itself a primer extension product. The term "first primer extension product" refers to molecule that are the product of extension of a primer. The term "second primer extension products" refers to the product obtained by extending first primer extension products. If the second primer extension products are sequenced, then the entire molecule (or most of it) may be sequenced, which sequence includes at least the sequence added onto the primer in the first primer extension reaction and sequence added onto the first primer extension product in the second primer extension reaction.

The term "hybridization" or "hybridizes" refers to a process in which a nucleic acid strand anneals to and forms a stable duplex, either a homoduplex or a heteroduplex, under normal hybridization conditions with a second complementary nucleic acid strand and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (sec, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions includes hybridization at about 42° C. in 50% formamide, 5×SSC, 5× Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by, e.g., Illumina, Life Technologies, BGI Genomics (Complete Genomics technology), and Roche etc. Next-generation sequencing methods may also include nanopore sequencing methods or electronic-detection based methods such as, e.g., Ion Torrent technology commercialized by Life Technologies.

The term "duplex," or "duplexed," as used herein, describes two complementary polynucleotides that are base-paired, i.e., hybridized together.

The terms "determining," "measuring," "evaluating," "assessing," "assaying," and "analyzing" are used interchangeably herein to refer to forms of measurement, and include determining if an element is present or not. These terms include both quantitative and/or qualitative determinations. Assessing may be relative or absolute.

The term "ligating", as used herein, refers to the enzymatically catalyzed joining of the terminal nucleotide at the 5' end of a first DNA molecule to the terminal nucleotide at the 3' end of a second DNA molecule.

The terms "plurality", "set" and "population" are used interchangeably to refer to something that contains at least 2 members. In certain cases, a plurality may have at least 10, at least 100, at least 1000, at least 10,000, or at least 100,000 members.

A "primer binding site" refers to a site to which an oligonucleotide hybridizes in a target polynucleotide or fragment. If an oligonucleotide "provides" a binding site for a primer, then the primer may hybridize to that oligonucleotide or its complement.

The term "strand" as used herein refers to a nucleic acid made up of nucleotides covalently linked together by covalent bonds, e.g., phosphodiester bonds.

The term "extending", as used herein, refers to the extension of a nucleic acid by ligation or the addition of nucleotides using a polymerase. If a nucleic acid that is annealed to a polynucleotide is extended, the polynucleotide acts as a template for an extension reaction. In these embodiments, the nucleic acid may be extended by a template-dependent polymerase or by ligation to an oligonucleotide that is complementary to the polynucleotide, where the polynucleotide acts as a splint.

The term "extending" includes extension at the 3' end or the 5' end. Primer extension, ligation and gap-fill ligation reactions are types of extending.

The term "extendible 5' or 3' end" refers to a 5' phosphate and 3' hydroxyl, respectively, both of which are extensible by ligation. 3' hydroxyls are also extendible by a polymerase.

The term "as a template" as used herein, refers to: (a) a primer extension reaction in one strand acts as a template for the addition of nucleotides by a polymerase, (b) a splinted ligation, where one strands acts a template (or "splint") for ligating two nucleic acid molecules together. In ligation reactions, both molecules hybridize to the template and become ligated. Ligation can be at the 5' end of a nucleic acid molecule or at the 3' end of a nucleic acid molecule. at the 3' end or the 5' end; and (c) gap-fill/ligation reactions. In gap-fill/ligation reactions, two nucleic acids are hybridized to a template with a gap inbetween. One nucleic acid molecule is extended towards the other nucleic acid molecule by primer extension and then the 3' end of product is ligated to the other nucleic acid. As used herein, the term "rolling circle amplification" or "RCA" for short refers to an isothermal amplification that generates linear concatemerized copies of a circular nucleic acid template using a strand-displacing polymerase. RCA is well known in the molecular biology arts and is described in a variety of publications including, but not limited to Lizardi et al (Nat. Genet. 1998 19:225-232), Schweitzer et al (Proc. Natl. Acad. Sci. 2000 97:10113-10119), Wiltshire et al (Clin. Chem. 2000 46:1990-1993) and Schweitzer et al (Curr. Opin. Biotech 2001 12:21-27), which are incorporated by reference herein.

As used herein, the term "rolling circle amplification products" refers to the concatemerized products of a rolling circle amplification reaction.

As used herein, the term "surface" refers to any solid material (e.g. glass, metal, ceramics, organic polymer surface or gel) that may contain cells or any combinations of biomolecules derived from cells, such as proteins, nucleic acids, lipids, oligo/polysaccharides, biomolecule complexes, cellular organelles, cellular debris or excretions (exosomes, microvesicles), etc. Tissue blots, western blots and glass slides are examples of solid materials that have a surface. Cells, e.g., suspensions of mammalian cells, are another example of a surface.

As used herein, the term "splint" refers to an oligonucleotide that hybridize to the ends of two other oligonucleotides and brings those ends together to produce a ligatable junction or a gap that can be filled by a gap-fill/ligation reaction.

As used herein, the term "barcoded particles" is intended to refer to both barcoded RCA products and barcoded nanoparticles, wherein the particles in a population of barcoded particles are each separately barcoded with a unique particle identifier sequence, i.e., a sequence that is unique to each particle such that the particles can be distinguished from one another by their unique identifier sequences.

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Before certain aspects of the present invention are described in greater detail, it is important to note that the figures illustrate embodiments of present probe system and method that employ RCA products. As noted below, the principles illustrated in the figures can be readily applied to barcoded nanoparticles and, as such, the present invention should not be limited to what is described in the figures. In addition, only one of the RCA product repeats is shown in the figures. As is well known, barcoded RCA products (and barcoded nanoparticles) may contain at least 10, at least 50, at least 100, at least 500 or at least 1,000 repeats of the molecule (which are either concatenated in the RCA product) or tethered to the surface of a nanoparticle).

Figure 2:
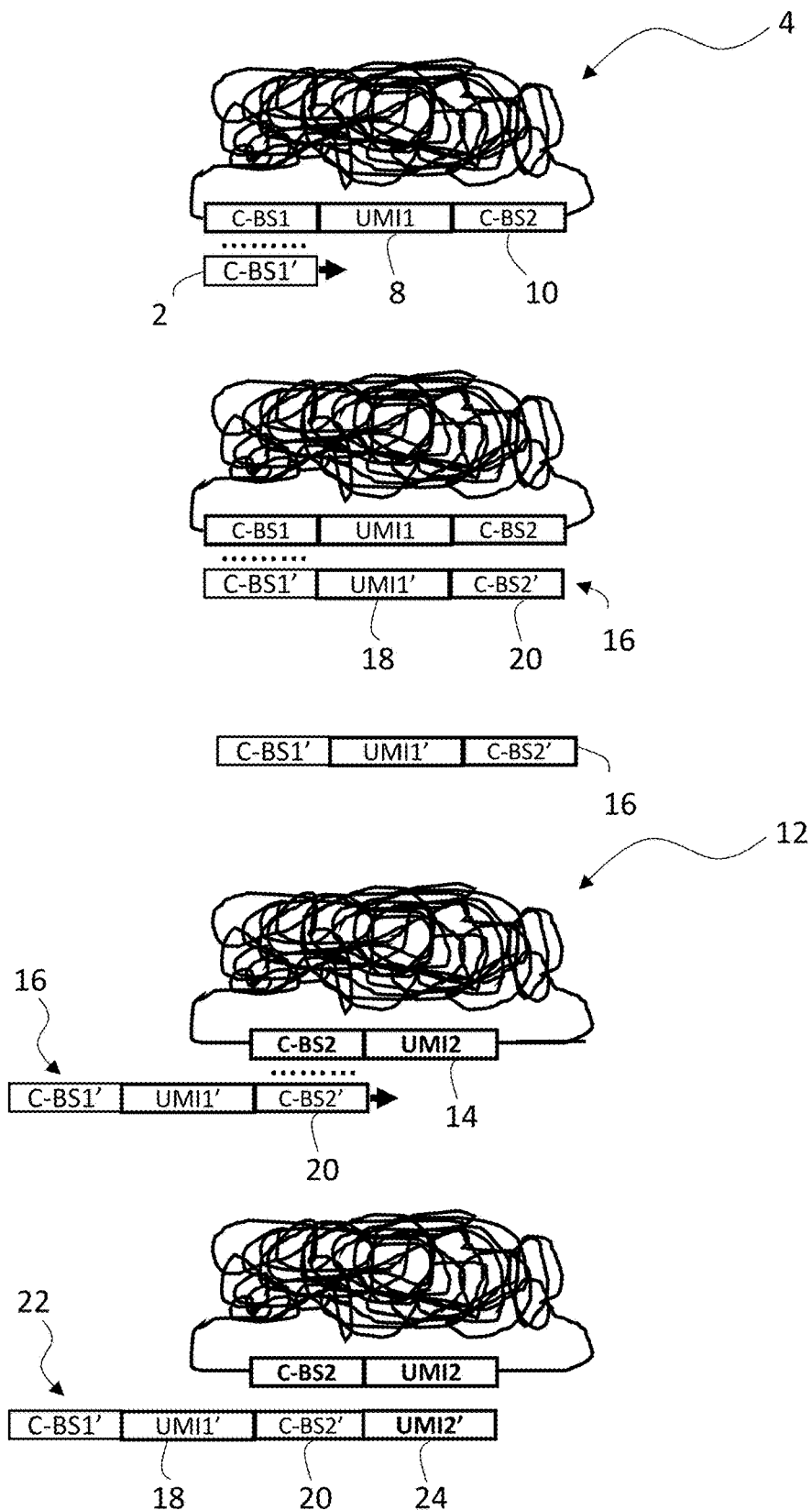
FIG. 2 schematically illustrates a method in which the probe system can be used.
Figure 12:
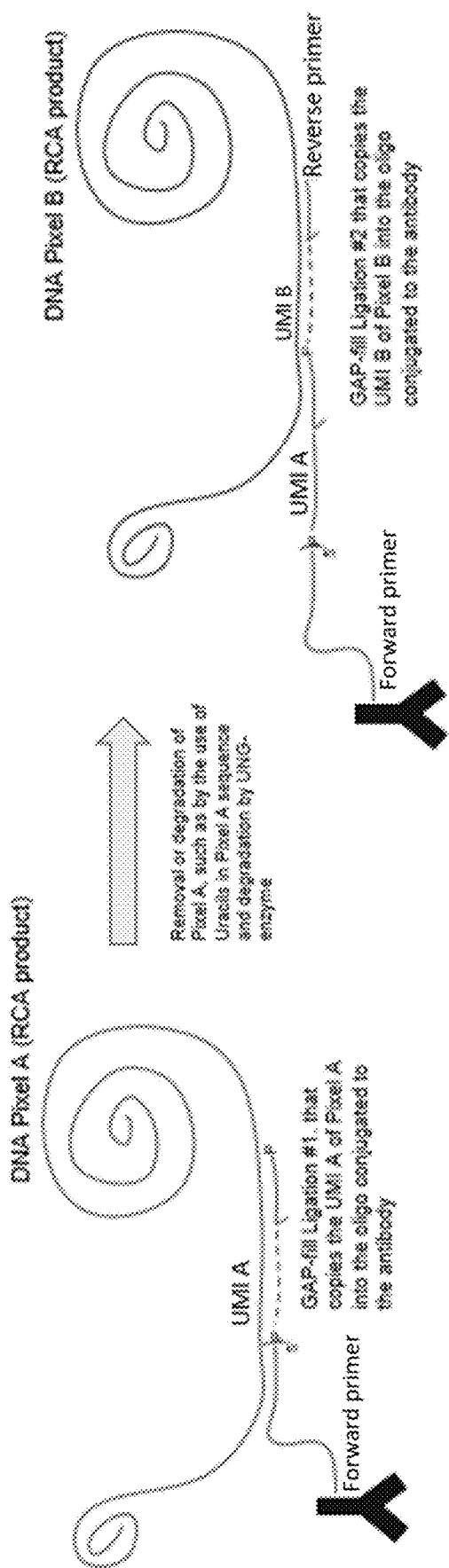
FIG. 12 schematically illustrates a gap-fill/ligation implementation of the present method.
Figure 13:
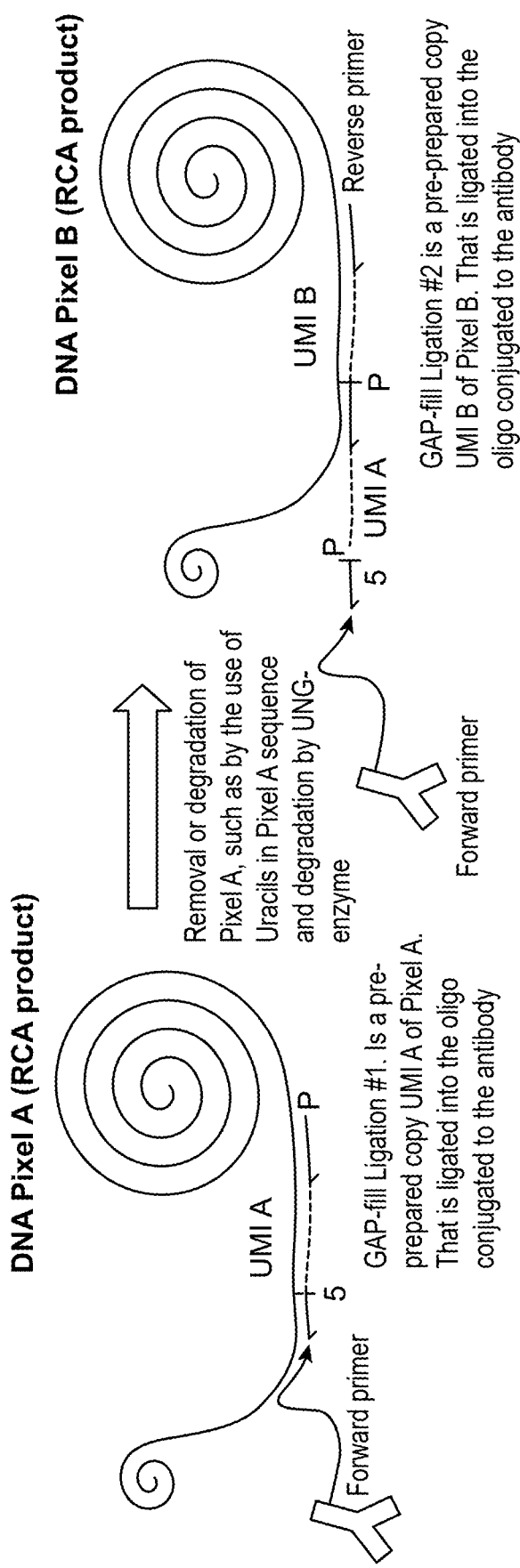
FIG. 13 schematically illustrates a ligation-based version of the present method, where the nucleic acid molecules are attached to "pre-made" barcodes.
Figure 14:
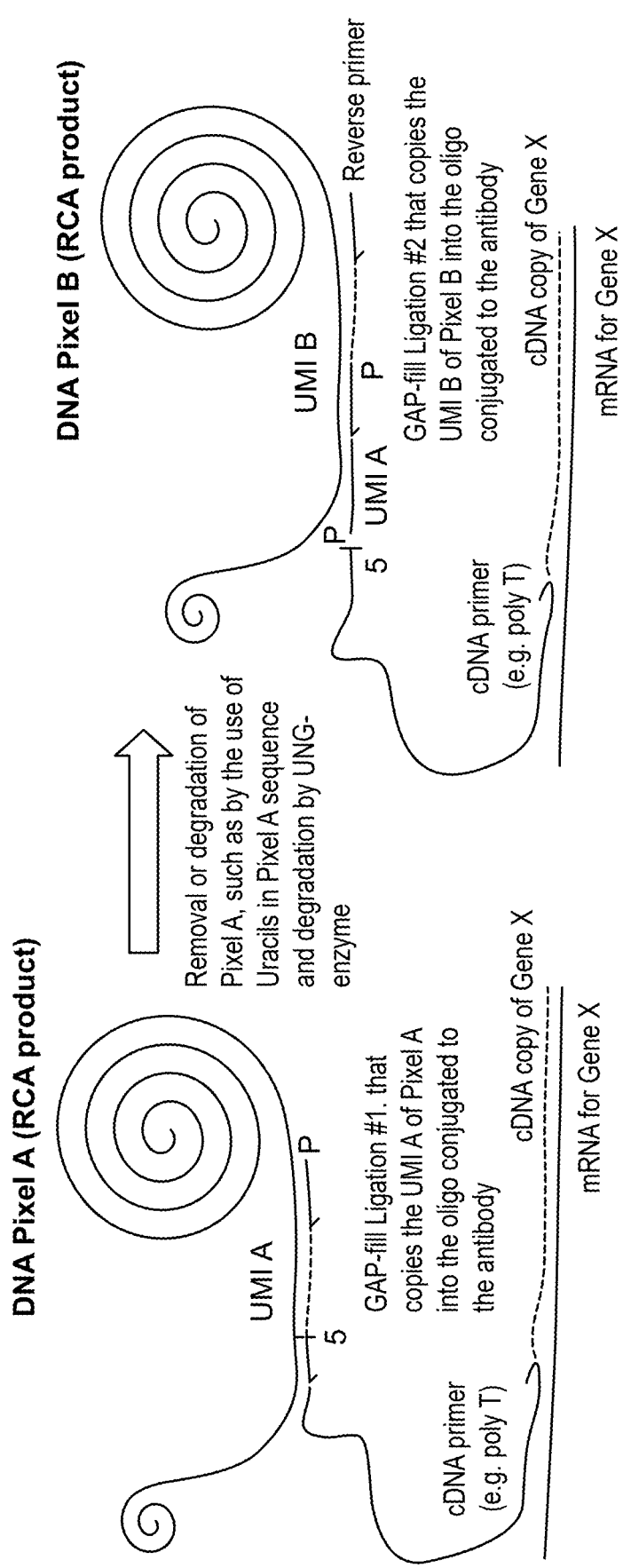
FIG. 14 schematically illustrates a gap-fill/ligation version of the present method that can be used to add barcodes to cDNA.

Moreover, it is recognized that the present probe system and method does not need to be implemented as a primer extension assay (as illustrated in FIG. 2). As illustrated in FIGS. 12-14, the method may be implemented using gap-fill/ligation or ligation assay, which can both involve extending the 5' end of the nucleic acid molecules using the barcoded particles as a template. As such, while the description below is focused on embodiments, that employ primer extension, it should be recognized that the primer extension-based embodiments described below are just an example of how the method can be implemented.

Some principles of the present probe system are illustrated in FIG. 1. With reference to FIG. 1, the probe system may comprise: a population of primer molecules 2 (which, as shown, have a 3' end of sequence C-BS1'). As will be described in greater detail below, the primer molecules may be synthetic oligonucleotides or cDNA molecules that have a primer sequence at the 3' end, for example. In some embodiments, the primer molecule may be linked to a binding agent (e.g., an oligonucleotide probe, antibody, aptamer, etc.) and in other embodiments, the primer molecules may be linked to a planar substrate as a lawn in which the 3' ends of the oligonucleotides are distal to the substrate and capable of being extended by a polymerase. As illustrated, the probe system also comprises first set of barcoded particles 4 and second set of barcoded particles 12. As shown, the particles in the first set of barcoded particles 4 each have a nucleotide sequence comprising: a primer binding sequence 6 (C-BS1) that is complementary to the 3' end of the primer molecules 2, as well as a unique particle identifier sequence 8 (UMI1), and first template sequence 10 (C-BS2). The particles in the second set of barcoded particles 12 each have a nucleotide sequence comprising: the first template sequence 10 (i.e., the same template sequence as is in the first set of particles, C-BS2), and a unique particle identifier sequence 14 (UMI2). In the embodiment shown, the nucleotide sequence of the second set of barcoded particles does not contain primer binding sequence 6 (CBS1). However, in other embodiments, the nucleotide sequence of the second set of barcoded particles may contain primer binding sequence 6 (CBS1). In this probe system (as shown in FIG. 2), extension of the primer molecules 2 using the first set of barcoded particles 4 as a template produces first primer extensions products 16 that contain the complement of a unique particle identifier sequence 18 of a particle of the first set of barcoded particles (i.e., the complement of UMI1, or UMI1') and the complement 20 of the first template sequence (C-BS2', which is the complement of C-BS2). As will be described in greater detail below, the 3' end of the primer extension product 16 can hybridize to the first template sequence 10 of the second set of particles. As shown, extension of the 3' end of the primer extension product 16 using a particle from the second set of barcoded particles as a template results in second primer extension products 22 that contain the complement 18 of a unique particle identifier sequence from the first set of particles, the complement 20 of the first template sequence, and 24 the complement of a unique particle identifier sequence from the second set of particles. In some embodiments, there may be an internal hairpin immediately downstream of first template sequence.

In some embodiments, the first and second sets of barcoded particles may be rolling circle amplification (RCA) products or barcoded nanoparticles. For example, in some embodiments, the first and second sets of barcoded particles may be RCA products, the first and second sets of barcoded particles may be barcoded nanoparticles or the first set of barcoded particles may be RCA products or barcoded nanoparticles and the second set of barcoded particles may be the other type.

In embodiments in which the barcoded particles are RCA products, the RCA products each contain a unique sequence that is in the repeated sequence. In other words, if there are 1,000 RCA products, each product will have a unique sequence (referred to herein as a unique molecular identifier "UMI" or unique identifier "UID"). The UID for one particle is different to the UIDs for other particles. The RCA product can be made by, e.g., synthesizing initial oligonucleotides that have a degenerate sequence, circularizing the initial oligonucleotides using a splint, and amplifying the circularized oligonucleotides by RCA. In some embodiments, the initial oligonucleotides may contain a degenerate (e.g., random) sequence of 6-10 nucleotides, or even more random nucleotides dependent on the number of unique RCA products required. Amplification of circularized oligonucleotides that have a degenerate sequence should produce a population of RCA products that each have a unique identifier (i.e., a sequence that is different from the other RCA products in the population). Methods for generating RCA products that have unique identifiers are described in Wu et al (Nat. Comm. 2019 10:3854) and US20160281134, for example, and are readily adapted for use herein. In some embodiments, the different oligonucleotides that are used to make the first and second sets of RCA products are made separately and then mixed together. In other embodiments, the different oligonucleotides may be made in parallel on a planar support in the form of an array and then cleaved from the array. Examples of such methods are described in, e.g., Cleary et al. (Nature Methods 2004 1:241-248) and LeProust et al. (Nucleic Acids Research 2010 38:2522-2540). In some embodiments, one or both sets of RCA products may contain uracil of thymine, thereby allowing the RCA products to be degraded enzymatically, by USER (sec, e.g., Bitinaite et al Nucleic Acids Res. 2007 35:1992-2002), which contains UDG (uracil DNA glycosylase) and an AP lyase which cleaves the phophodiester backbone at apurinic sites.

In embodiments in which the barcoded particles are barcoded nanoparticles, the barcoded nanoparticles are small beads or metallic particles the like, that are coated in oligonucleotides, where the surface-tethered oligonucleotides on each particle have a unique sequence that is different to the sequence that is in the oligonucleotides that are tethered to other particles in the population. In other words, if there are 1,000 barcoded particles, the oligonucleotides that are tethered to each particle will have a unique sequence (referred to herein as a unique molecular identifier "UMI" or unique identifier "UID". The UID for one particle is different to the UIDs for other particles. These particles can be of any suitable size, material and shape. In many embodiments, the particles have a size of 10 nm-200 nm. Gold particles (that can be readily made to any diameter in the range of 1.8 nm to 1500 nm, for example) can be used, although the particles can also be made from silver, silica, titanium dioxide, carbon, polymers (like polystyrene, polyacrylate, etc), agarose, etc. Magnetic particles of iron and various alloys could also be used (Creative Diagnostics, Shirley, NY, USA). The particles do not need to be magnetic, but magnetic nanospheres could be used in some cases (Creative Diagnostics, Shirley, NY, USA). There are several surface chemistries for functionalizing metal surfaces so that they can be joined to nucleic acid. For example, the particles may be modified to contain reactive groups, including, but not limited to, N-hydroxysuccinimidyl ester, sulfo-N-hydroxysuccinimidyl ester, a halo-substituted phenol ester, pentafluorophenol ester, a nitro-substituted phenol ester, an anhydride, isocyanate, isothiocyanate, an imidoester, maleimide, iodoacetyl, hydrazide, an aldehyde, or an epoxide. Other suitable groups are known in the art and may be described in, e.g., Hermanson, "Bioconjugate Techniques" Academic Press, 2nd Ed., 2008. The most commonly used capture-agent reactive groups are NHS (which is amine-reactive) and maleimide (which is sulfhydryl-reactive), although many others may be used. The particles can also be coated in streptavidin, which can bind to biotinylated nucleic acids. In some embodiments, the barcoded particles may be made by emulsion PCR, which method has been successfully used for other applications and is described in, e.g., Kanagal-Shamanna et al (Methods Mol Biol 2016 1392:33-42) and Shao et al (PlosOne 2011 0024910). In some embodiments, the nucleic acids of the barcoded particles may contain uracil, thereby allowing them to be cleaved using USER, as discussed above.

In any embodiment, the primer molecules 2 may contain a 5' tail that does not hybridize to any of the nucleic acids of the barcoded particles. The 5' tail may contain a primer binding site (e.g., for a forward primer) and a target identifier sequence which may be used later in the protocol. As noted above, the primer molecules may be synthetic, man-made oligonucleotides that are in the 10-200 nucleotides in length. In some of these embodiments, the primer molecules may be linked to a binding agent, (e.g., an oligonucleotide probe, antibody, aptamer, etc.). In these embodiments, the primer molecules are not cDNA. In some embodiments, the primer molecules may contain cDNA molecules that have a primer sequence at the 3' end, i.e., an appended sequence that can serve as a primer. In these embodiments, the cDNA can be made by, e.g., hybridizing a reverse transcription primer (e.g., a primer that has a 3' end made of oligo (dT), a random sequence or gene-specific sequence, that may optionally have a 5' end that does not hybridize to the RNA and may contain a sequence that provides a binding site for a PCR primer) to RNA, e.g., RNA that is in sample in situ. The reverse transcription primer can be extended in situ (in a reaction that contains NTPs, reverse transcriptase and any other necessary reagents) to produce cDNA products to produce the first strand cDNA. The primer sequence may be added to the cDNA by template switching (sec, e.g., Zhu et al BioTechniques 2001 30:892-7), ligation a 3' adapter or by tailing, e.g., by a terminal transferase. As indicated above, in cDNA embodiments, the cDNA may be made in situ and, as such, the primer may be in or on a tissue section. In other embodiments, the primer molecules may linked to a planar substrate, e.g., via their 5' ends such that they form a "lawn".

In embodiments in which the primer molecules may be linked to a binding agent, the binding agent may be an oligonucleotide probe, an antibody, or an aptamer, for example. In these embodiments, the primer molecules may additionally contain a sequence that identifies the target to which the binding agent binds. For example, if the primer is linked to an antibody, the primer may additionally contain a target identifier sequence that identifies the antibody name or the target (e.g., epitope) to which the antibody binds to in the 5' end of the primer (downstream from any primer sequences). As such, in some embodiments, the primer may be part of a capture agent-primer conjugate in which a capture agent, e.g., an antibody or aptamer and primer that are linked non-covalently (e.g., via a streptavidin/biotin interaction) or covalently (e.g., via a click reaction or the like) linked to a single-stranded primer in a way that the capture agent can still bind to its binding site. The oligonucleotide and the capture agent may be linked via a number of different methods, including those that use maleimide or halogen-containing group, which are cysteine-reactive. The capture agent and the oligonucleotide may be linked proximal to or at the 5' end of the oligonucleotide, proximal to or at the 3' end of the oligonucleotide, or anywhere in-between. In some embodiments, the oligonucleotides may be linked to the capture agents by a linker that spaces the oligonucleotide from the capture agents. Oligonucleotides may be linked to capture agents using any convenient method (see, e.g., Gong et al., Bioconjugate Chem. 2016 27:217-225 and Kazane et al. Proc Natl Acad Sci 2012 109:3731-3736). As noted above, the sequence of a primer that is conjugated to a binding agent uniquely identifies the epitope or sequence to which the binding agent binds. For example, if the method is performed using 10 different antibodies, then each antibody is tethered to a different primer that contains a sequence that identifies the epitope to which the antibody binds. This feature allows the method to be multiplexed and, in some embodiments, at least 5, at least 10, at least 20 or at least 50 different antibodies that bind to different markers in or on the surface of a cell can be used in the method. Each antibody is conjugated to a different target identifier sequence, and the antibody identifier sequences allow the binding events for a particular antibody to be mapped. Such tagged antibodies are described in, e.g., Wu et al (Nat. Comm. 2019 10:3854) and US20160281134, and others.

In embodiments in which the primer molecules may be linked to a planar substrate, the substrate may be made by, e.g., making the primer molecules synthetically, e.g., using phosphoramidite chemistry and tethering the primer molecules to a planar support, e.g., a glass slide or the like, by the 5' end, the chemistry for which is well known.

Figure 3:
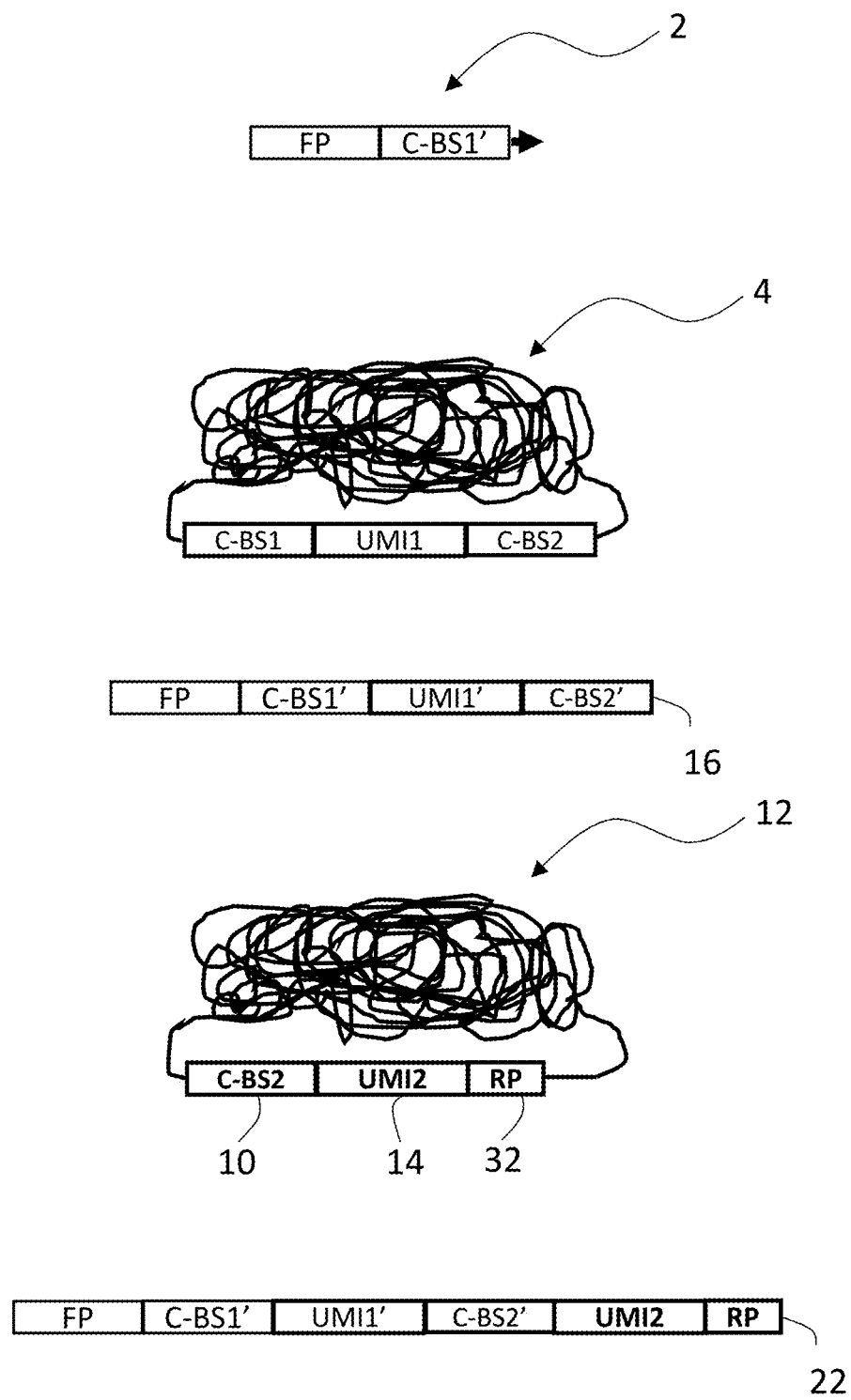
FIG. 3 schematically illustrates a probe system that has primer binding sites, thereby allowing the extension products to be amplified.
Figure 4:
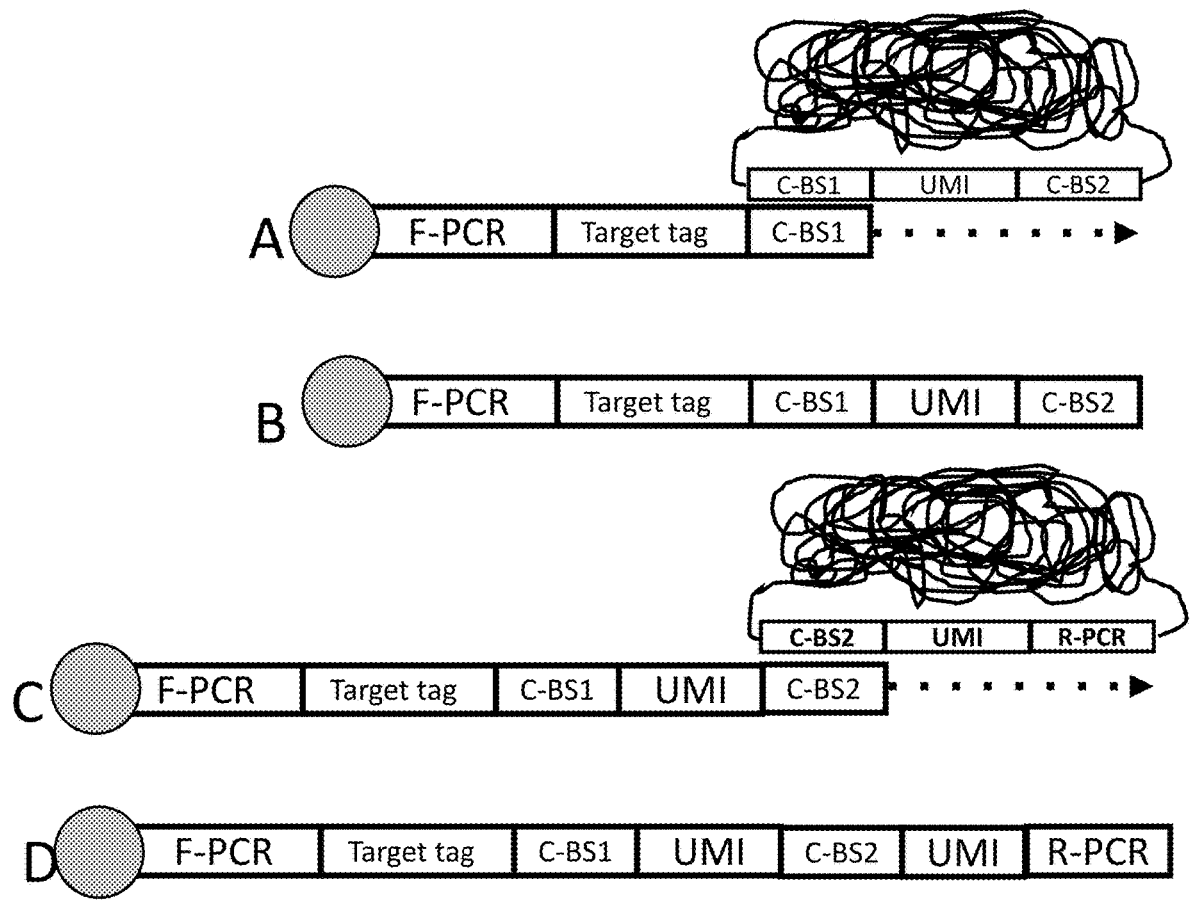
FIG. 4 schematically illustrates an embodiment of the method in which the primers are teghered.

In any embodiment, the primer molecules 2 may have a 5' tail that has a forward primer sequence 30 and the nucleotide sequence of the second set of barcoded particles 12 has a reverse primer sequence 32 downstream of the unique particle identifier sequence 14, as illustrated in FIG. 3. In this embodiment (and as illustrated in FIG. 4) the second primer extension product has forward and reverse primer sequences, thereby allowing the product to be amplified by PCR.

The lengths of the component parts of a nucleic acid molecule described herein may vary. In some embodiments, the part of the primer that hybridizes to the primer binding sequence 6 (C-BS1) may be at least 10 nucleotides in length, e.g., 12-50 nucleotides in length, the UMI sequences may be at least 5 nucleotides in length, e.g., 6-20 nucleotides in length, and the first template sequence 10 may be at least 10 nucleotides in length, e.g., 12-50 nucleotides in length.

In any embodiment, the first and second sets of barcoded particles may each comprise at least 10 members (e.g., at least 100, at least 1,000, at least 10,000, at least 100,000, at least IM at least 10 M, at least 100 M, at least 1B or at least 10B members), which are each uniquely identifiable by their particle identifier sequence. In some embodiments, the nucleic acid sequences of the barcoded particles in the first and second sets of barcoded particles may be identical to one another except for their particle identifier sequences.

Figure 15:
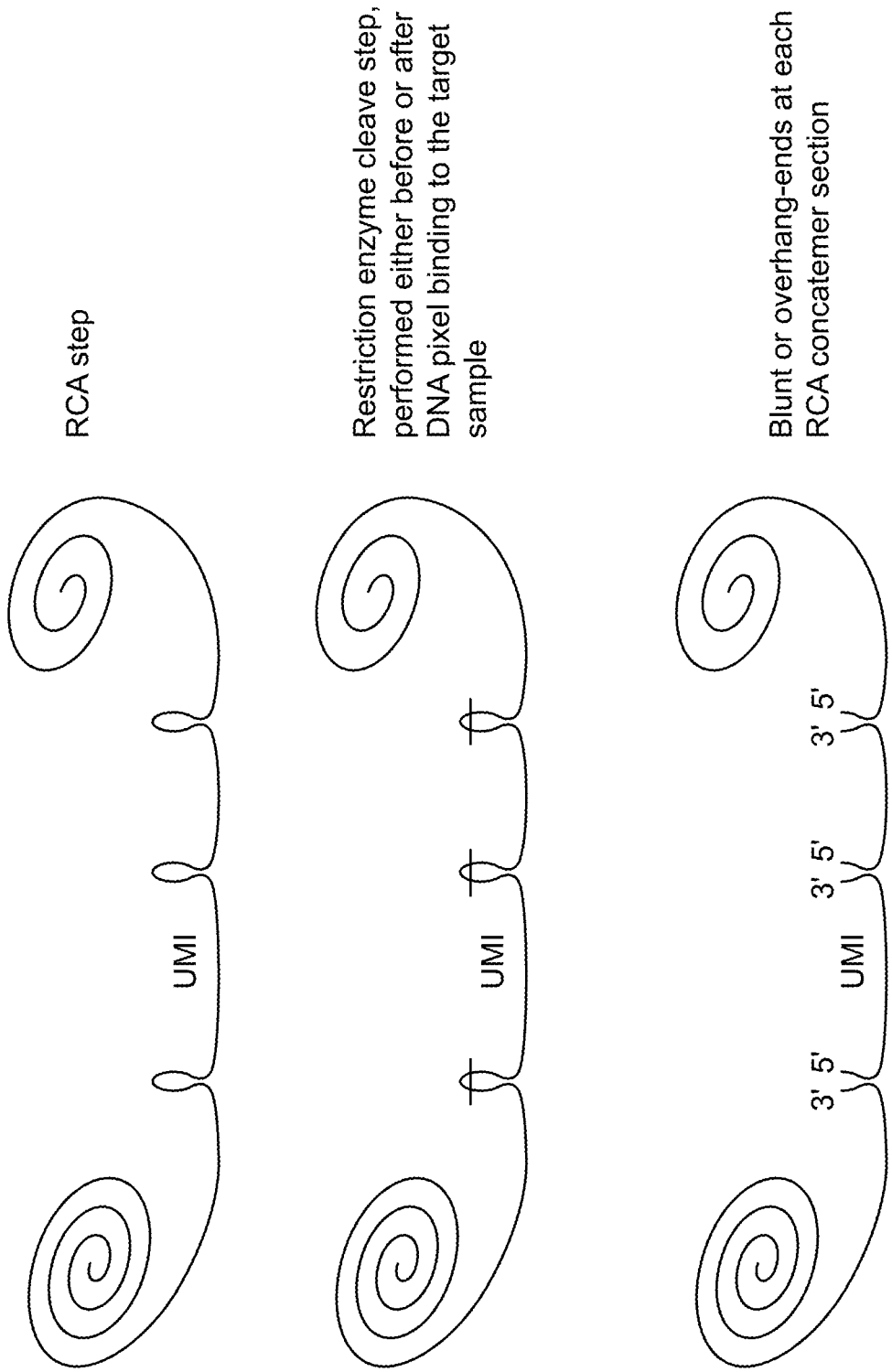
FIG. 15 schematically illustrates how the method can be implemented using rolling circle amplification products using a hairpin in each of the repeats.
Figure 16:
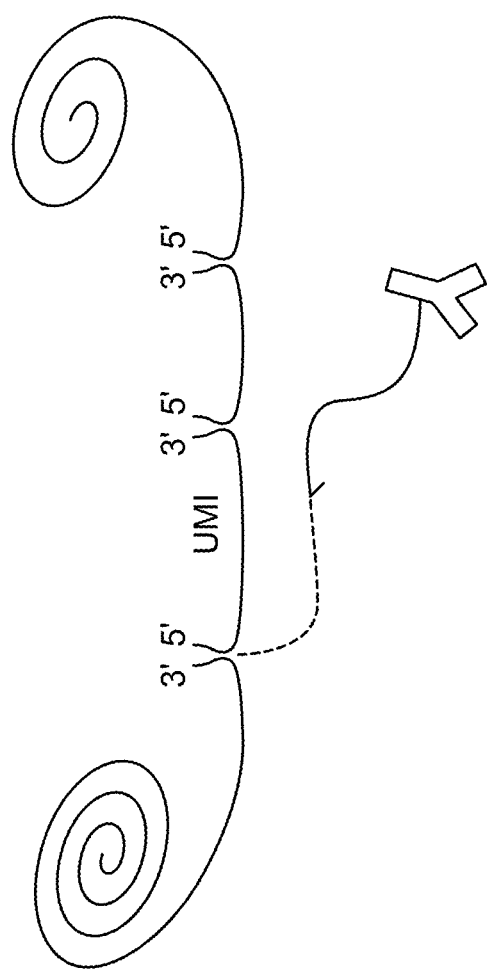
FIG. 16 follows on from FIG. 15 and illustrates one example of the assay can be designed so that the primer extension product end at a defined nucleotide, thereby allowing it to be used as a primer in the next step of the method.

A method for adding unique particle identifier sequences to a primer using the present probe system is also provided. The principle of this method is illustrated in FIG. 2. In these embodiments the method may comprise hybridizing the first set of barcoded particles 4 with the population of primer molecules 2, extending the hybridized primer molecules using the nucleotide sequence of the first set of barcoded particles as a template to produce first primer extension products 16 that contain i. the complement 18 of a unique particle identifier sequence from a barcoded particle in the first set of barcoded particles and ii. the complement 20 of the first template sequence. Next, the first set of barcoded particles are removed, e.g., denaturation and washing, or e.g. by having incorporated uracil residues in place of thymidine in the first barcoded particle and treating the product enzymatically, e.g., using USER (NEB), which contains uracil-n-glycosylase enzyme and an AP lyase, which is capable of cleaving phosphodiester bonds specifically at apurinic sites, thereby degrading the first barcoded particle liberating the extended primer, In these embodiments, primer 2 (and thus primer extension product 16) may be tethered to a support or a sample (e.g., via a capture agent) and, as such, the first set of barcoded particles can be subjected to stringent wash conditions without removing the primer or primer extension product from the sample or support. Further, the first primer extension product may be terminated at the correct position (i.e., at the end of the first template sequence) by either engineering a site for a restriction enzyme at that position and then digesting the primer extension products (which will be double stranded) with the restriction enzyme after they have been produced, or hybridizing a blocking oligonucleotide to a sequence immediately downstream from the first template sequence, or by designing an internal hairpin immediately downstream from the first template sequence, which will cause the polymerase to stall. In these latter embodiments, the polymerase (which should be a non-strand displacing polymerase) should terminate synthesis when it runs into the blocking oligonucleotide or hairpin. Alternative ways for terminating nucleic acid synthesis at defined sites are schematically illustrated in FIGS. 15-17. FIG. 15 illustrates RCA products that contain hairpin loops. These hairpin loops can cleaved by a restriction enzyme to liberate a 5' and 3' end either as blunt ends, or with overhang. FIG. 16 illustrates how a primer extension can be terminated at a defined site in the product. In this embodiment, the hairpins are digested to produce a blunt end or an overhang, but the RCA product stays together as a complex. The RCA products are then hybridize to the conjugated oligonucleotides and a strand displacing DNA polymerase (e.g. Klenow fragment of Ecoli DNA polymerase I) copies the barcode from the RCA product, displaces the hairpin, and terminates naturally as the template ends. That primer extension product can then be used as a primer on the next set of pixels. The restriction enzyme cleavage of the hairpin may be performed before or after the hybridization of the RCA products to the oligonucleotides. FIG. 17 illustrates how defined ends can be produced by digesting the extension products after they have been made, while they are still double-stranded.

Next, the method may comprise hybridizing the first primer extension products 16 with the second set of barcoded particles 12, wherein the complement 20 of the first template sequence in the first primer extension products hybridizes to the first template sequence in the second set of barcoded particles. Next, the method comprises extending the first primer extension products using the nucleotide sequence of the second set of barcoded particles as a template to produce second primer extension products that contain: a unique particle identifier sequence 18 from a barcoded particle in the first set of barcoded particles, the first template sequence 20, and a unique particle identifier sequence 20 from a barcoded particle in the second set of barcoded particles.

As illustrated in FIG. 3, the primer molecules 2 may have a forward primer sequence and the nucleotide sequence of the second set of barcoded particles 12 may have a reverse primer sequence downstream of the unique particle identifier sequence. In these embodiments, the first primer extension product 16 should contain the forward primer sequence at the 5' end, the second primer extension product 22 should contain the forward primer sequence at the 5' end and the reverse primer sequence at the 3' end. In this embodiment, the method may comprise amplifying the second primer extension products 22 by PCR using primers that target the forward and reverse primer sequences. FIG. 4 illustrates an embodiment of the method in which the primers are either tethered to a support or to a sample.

In some embodiments, the method may comprise sequencing the second primer extension products, or an amplified copy thereof. In these embodiments, each second primer extension product should contain the unique identifiers for two barcoded particles, thereby identifying which barcoded particles hybridized with the primer in the different hybridization steps. In some embodiments, and as will be described in greater detail below, the method may comprise mapping the relative positions of the primers using the pairs of unique particle identifier sequences that are in the second primer extension products.

As noted above, in some embodiments, the primers may be attached to a cellular sample via a binding agent. In these embodiments, the unique particle identifiers in the second primer extension products indicate the relative position of the binding agents on the cellular sample. This embodiment is illustrated in FIG. 4. As can be seen in FIG. 4, in these embodiments, the primer may include a target identification sequence. In the embodiments shown in FIG. 4, in steps A and B, the primer molecules contain a target identifier and are immobilized to the sample, e.g., via a binding agent. In this method, the first set of barcoded particles is hybridized to the sample and complements of the UMIs and C-BS2 sequence from the particles to which the primers are hybridized are copied onto the end of the primer molecules using the hybridized particles as templates. In steps C and D, the first set of barcoded particles is removed and the second set of particles are hybridized. After hybridization, the primer extension products are extended to add UMIs from the second set of particles onto the ends of the primer extension products. The pairs of barcodes that are copied onto the ends of the primers can be analyzed to determine the relative positions of different primers in the sample.

As indicated above, in alternative embodiments, the method may be implemented using a gap-fill/ligation and/or a ligation-based approach where, in these embodiments, the 5' end of a nucleic acid may be extended using the barcoded particles of (b) as a template by a gap-fill/ligation or ligation reaction. These embodiments are schematically illustrated in FIGS. 12-14. With reference to FIG. 12, instead of copying the barcodes from a barcoded particle by polymerizing from a free 3'end of an primer that is conjugated to a binding agent (as described above), a gap-fill/ligation reaction can be used to copy the barcode onto the 5' end of an oligonucleotide conjugated to the antibody, where the oligonucleotide has a 5' phosphate. These embodiments can be done using a combination of T4 DNA polymerase and T4 DNA ligase, for example. FIG. 13 shows how the 5' end or 3' end of an oligonucleotide that is conjugated to a binding agent can be ligated to a "pre-made" molecule that contains the barcode of a particle. In these embodiments, the barcodes are first copied by gap-fill/ligation reaction. During the assay itself, the oligonucleotide of the antibody is ligated to the 5' end or the 3' end of the pre-made copy of the barcode. In this figure, the 5' end of the oligonucleotide is ligated to the copy of the barcode, however this can be done the other way around, i.e., the oligonucleotides coupled to the antibody carry a free 3'end that is ligated to the 5'phosphate end of the UMI copy sequence. FIG. 14 illustrates how the 5' end of a cDNA can be added to a barcode via a gap-fill/ligation reaction. In this method, mRNA is copied in a a reverse transcription reaction (using an oligond (T) primer, a random primer or a gene-specific primer) and once the cDNA has been produced, the barcode is added to the 5' end of the cDNA via a gap-fill ligation reaction. These and other implementations can be envisioned.

Figure 5:
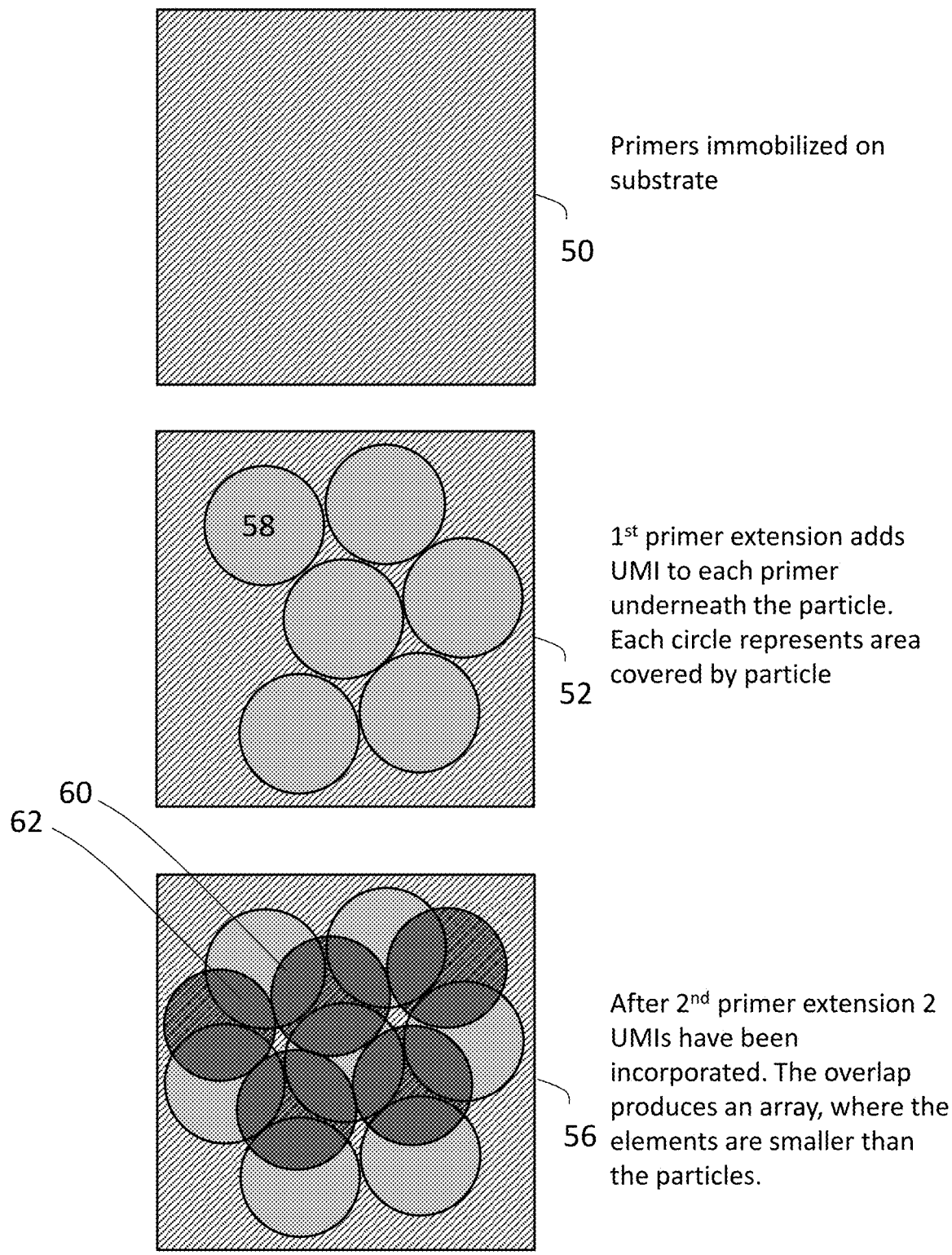
FIG. 5 schematically illustrates how the probe system can be used to produce an array.

As noted above, in some embodiments the primer molecules may be attached to a planar substrate, e.g., a glass slide or the like. In these embodiments, at least $10^6$, $10^7$, $10^8$ or $10^9$ primer molecules may be attached to a planar support and extended using the method described above. This method is schematically illustrated in FIG. 5. In this embodiment, the first and second sets of barcoded particles hybridize sequences that are in overlapping areas on the support 50. The first primer extension reaction adds the molecular identifiers to the primers that hybridize to the first set of barcoded particles to result in a first array of features 52 that correspond to the first primer extension products. In the example shown, there are six features 58, each corresponding to a barcoded particle and each containing a different molecular identifier. After the first primer extension reaction is completed, the first set of barcoded particles are removed and the second set of barcoded particles are hybridized to the substrate. In this step, the second set of barcoded particles hybridize with the first primer extension products, but in an overlapping manner to the first set of barcoded particles. Extension of the hybridized second set of barcoded particles adds the molecular identifiers from the second set of barcoded particles to the first primer extension products, to produce a second array of features 56 that that correspond to the second primer extension products. By way of example, in array 56, features 60 and 62 have the same unique identifier from a first barcoded particle (corresponding to feature 58) but different unique identifiers from the second barcoded particles.

Figure 6:
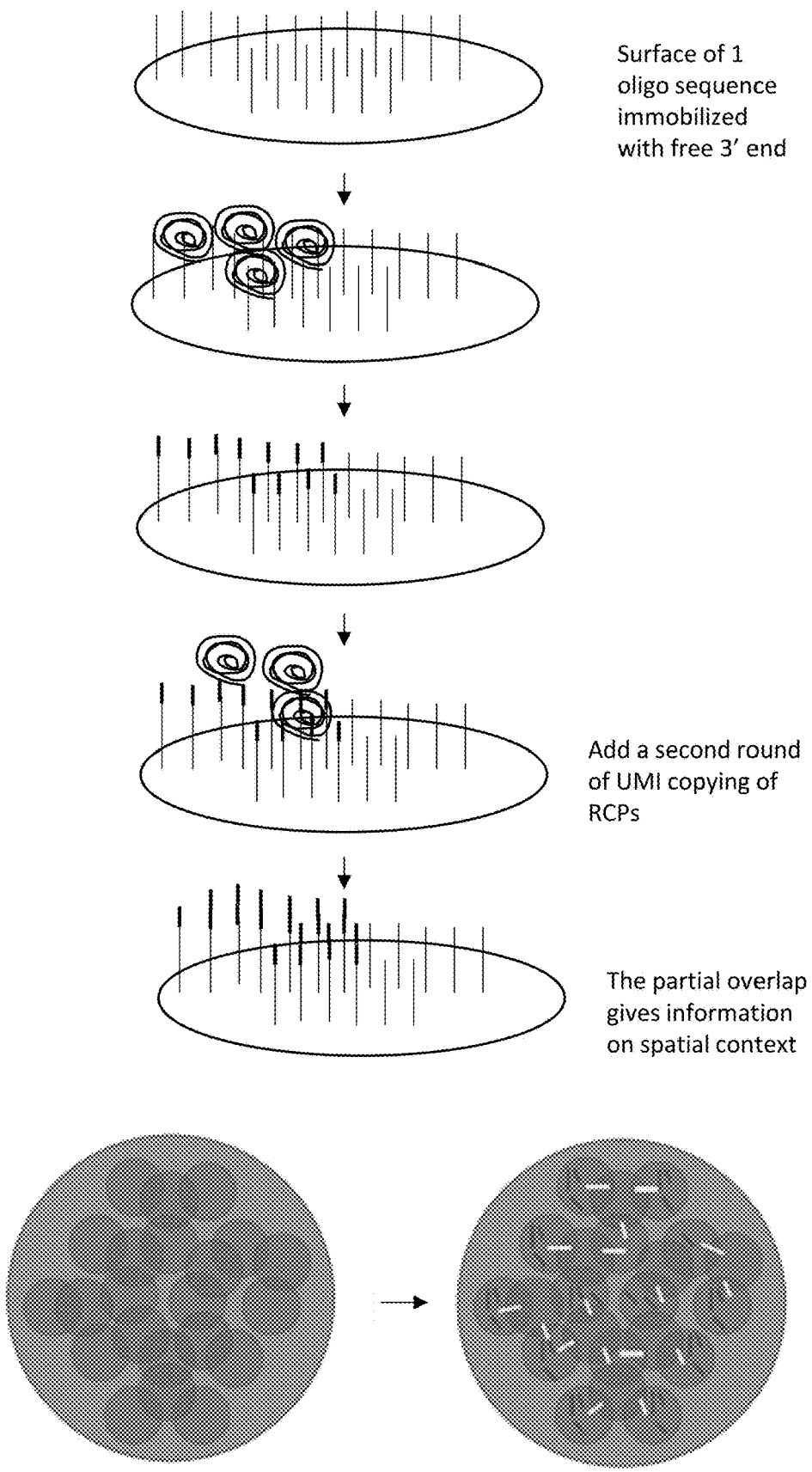
FIG. 6 also illustrates how the probe system can be used to produce an array.
Figure 7:
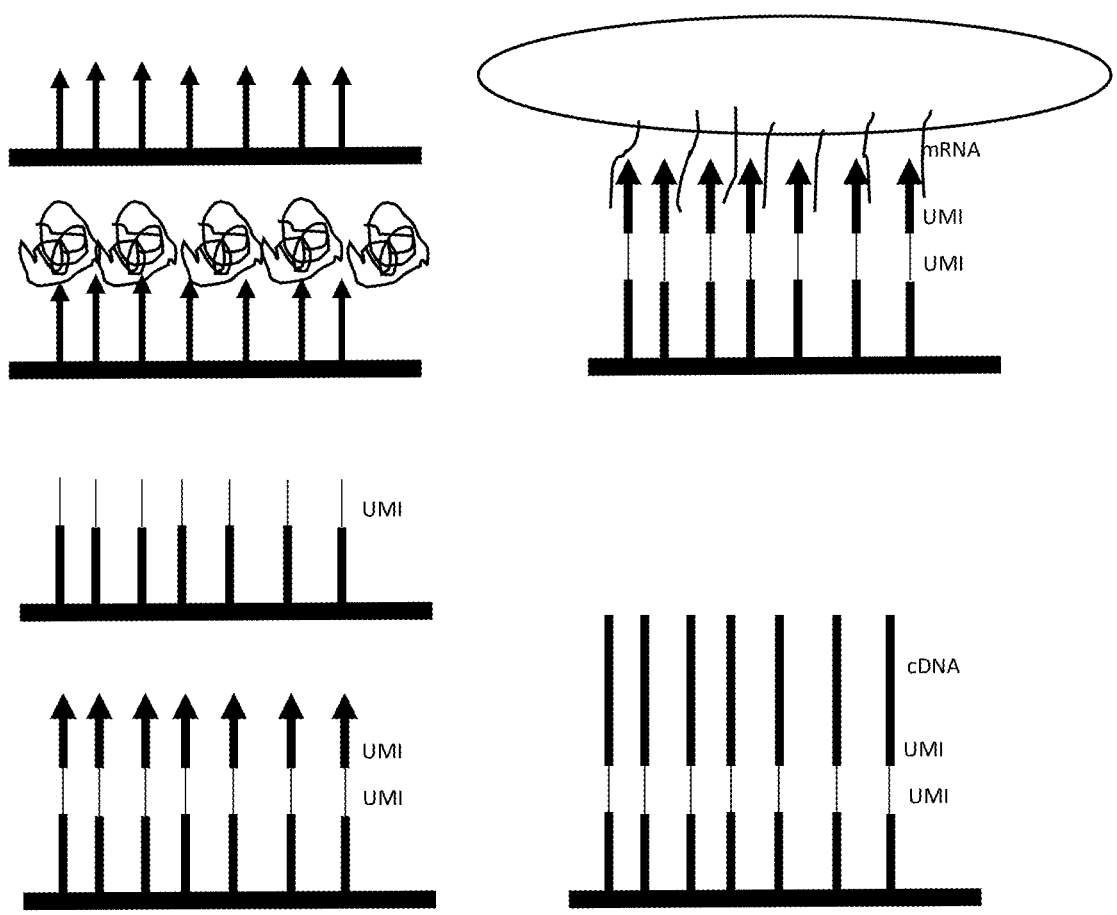
FIG. 7 illustrates how a sample can be analyzed using the array illustrated in FIGS. 5 and 6.

This embodiment of the method, which results in an array, is also illustrated in FIG. 6. With reference to FIG. 6, the method may start with a solid surface with an immobilized oligonucleotide. In Step 1, the free 3' ends of the immobilized oligonucleotides are extended into the first set of barcoded particles (e.g., RCA products) that have unique molecular identifiers. This extension step copies the complement of the unique molecular identifiers from the first set of barcoded particles onto the oligonucleotides. The barcoded particles are then removed. In Step 2, a second set of barcoded particles is added to the surface, effectively adding a second random barcode to the surface. The primer extension products are then extended =, which incorporate the identifiers of the second set of particles into the initial extension products. The second identifiers provide information on which first identifiers are in proximity. As the second addition has only partial overlap with the first, it will result in a spatial map of linked identifiers, illustrated at the bottom of FIG. 6. The array can then be used to capture biomolecules bound in a cell or a tissue sample, thereby providing spatial information of the biomolecules. The resolution will likely be at the size of the particle, which may be 50-500 nm, vastly surpassing the resolution of other methods. Alternatively, the capture of biomolecules in the sample (for example mRNA binding probes or poly A primers for cDNA) can be done on the surface containing the immobilized oligonucleotides (before primer extension). An example of the use of such an array is shown in FIG. 7.

Figure 8:
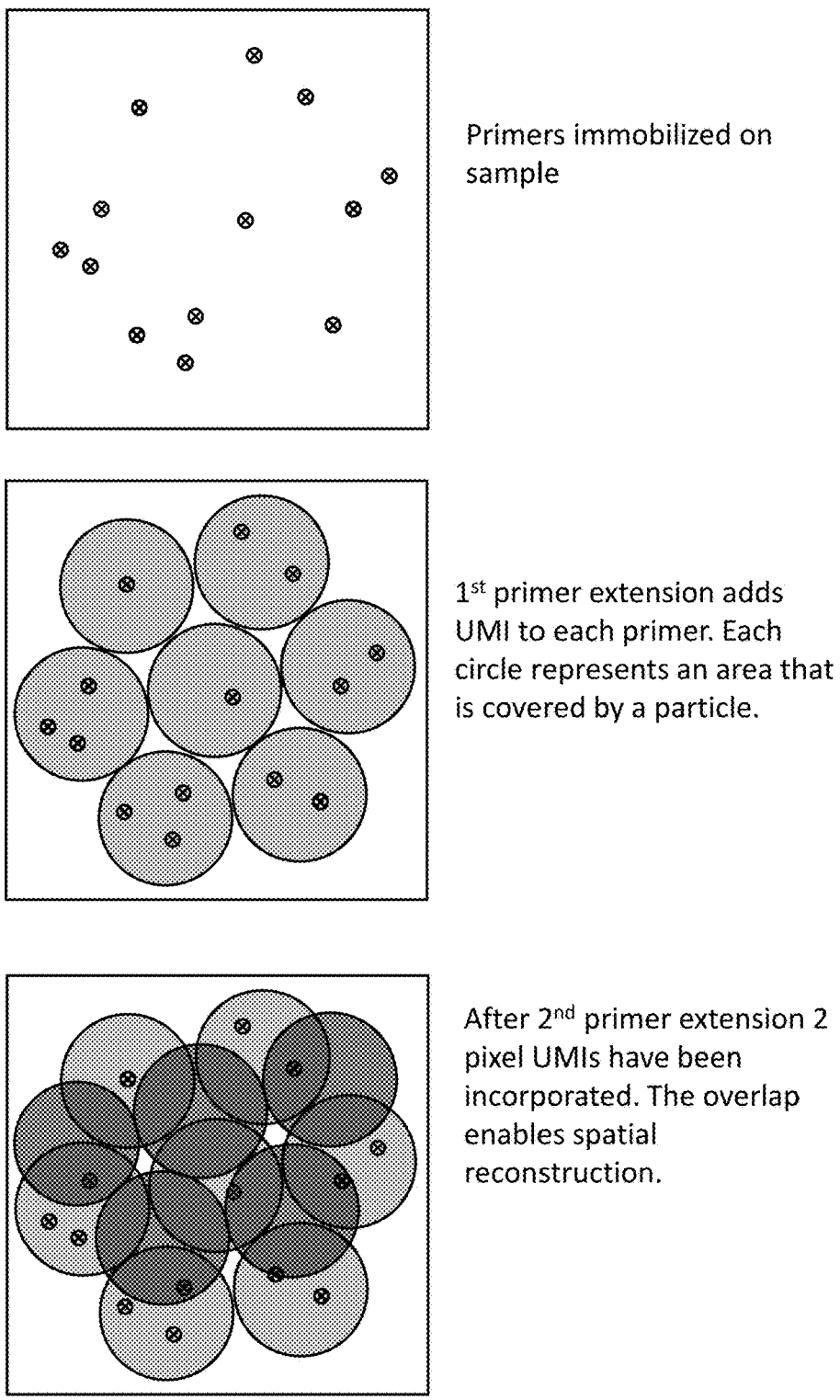
FIG. 8 schematically illustrates how binding sites can be spatially reconstructed.

The present probe system may be used to map binding events that are in or on a cellular sample. This method is schematically illustrated in FIG. 8. In these embodiments, the method may comprise obtaining a sample containing primer molecules that are bound to sites in or on cells. For example, as described above, this sample may be made by binding primers that are attached to binding agents (e.g., oligonucleotide probes, antibodies or aptamers) to sites that are in or on the cells, or by hybridizing a first primer to RNA in the cell, extending the primer to make cDNA, and appending a second primer onto the 5' end of the cDNA, where the cDNA becomes the primer molecules that are used in the present method. Other components used in the method include a first set of barcoded particles as discussed above, i.e., particles that that each have a nucleotide sequence comprising: a primer binding sequence that is complementary to the 3' end of the primer molecules, a unique particle identifier sequence, and a first template sequence, as illustrated in FIG. 1, as well as a second set of barcoded particles that each have a nucleotide sequence comprising: the first template sequence, and a unique particle identifier sequence, as illustrated in FIG. 1. In any embodiment and as illustrated in FIG. 1, the nucleotide sequence of the second set of barcoded particles may lack the primer binding sequence that is in the nucleotide sequence of the first set of barcoded particles. As such, in any embodiment, the nucleotide sequence of the second set of barcoded particles may lack the primer binding sequence that is in the nucleotide sequence of the first set of barcoded particles may comprise the first template sequence and a unique particle identifier sequence, but not the primer binding sequence that is in the nucleotide sequence of the first set of barcoded particles.

As described above, this method involves specifically hybridizing the first set of barcoded particles with the sample, wherein the nucleotide sequence of at least some of the first set of barcoded particles hybridizes to at least two primer molecules. The number of primer molecules that hybridize to each barcoded particle may vary, as shown in FIG. 8. Some of the first set of barcoded particles may hybridize to one primer molecule, but many should hybridize to at least two, at least 5, at least 10, or at least 20 primer molecules, depending on the density of the primer molecules and the size of the particles used. As with the method described above, the method comprises extending the primers that are hybridized to the barcoded particles using the nucleotide sequences to which the primers are hybridized as a template to produce first primer extension products that each comprise a first unique particle identifier sequence. Next, the method may comprise removing the first set of barcoded particles from the sample, as described above, and specifically hybridizing the second set of barcoded particles with the first primer extension products. In this step of the method the nucleotide sequences of at least some of the second set of barcoded particles hybridizes to at least two molecules of the primer extension products. Likewise, extending the first primer extension products that are hybridized to a barcoded particle in the prior using the nucleotide sequences to which the primers are hybridized as a template to produces second primer extension products that comprise the two unique particle identifier sequences, one from a particle in the first set, and another from a particle in the second set. Next, the method comprises determining which unique particle identifier sequence or complements thereof are in second primer extension products and making a map of the relative positions of the primers of using the unique particle identifier sequences that are in the second primer extension products.

Figure 9A:
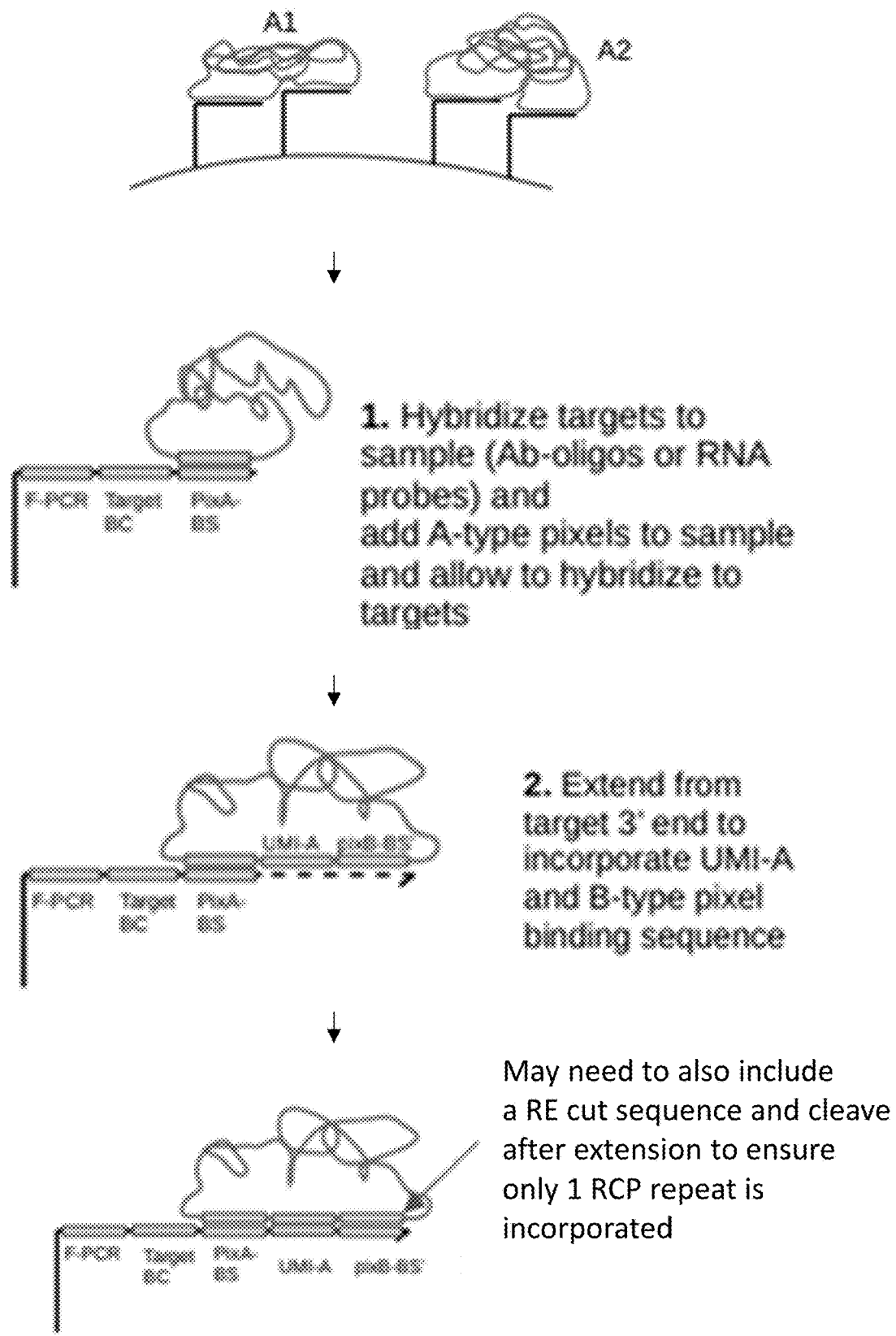
FIGS. 9A-9C schematically illustrate further details of an embodiment of the present method.
Figure 9B:
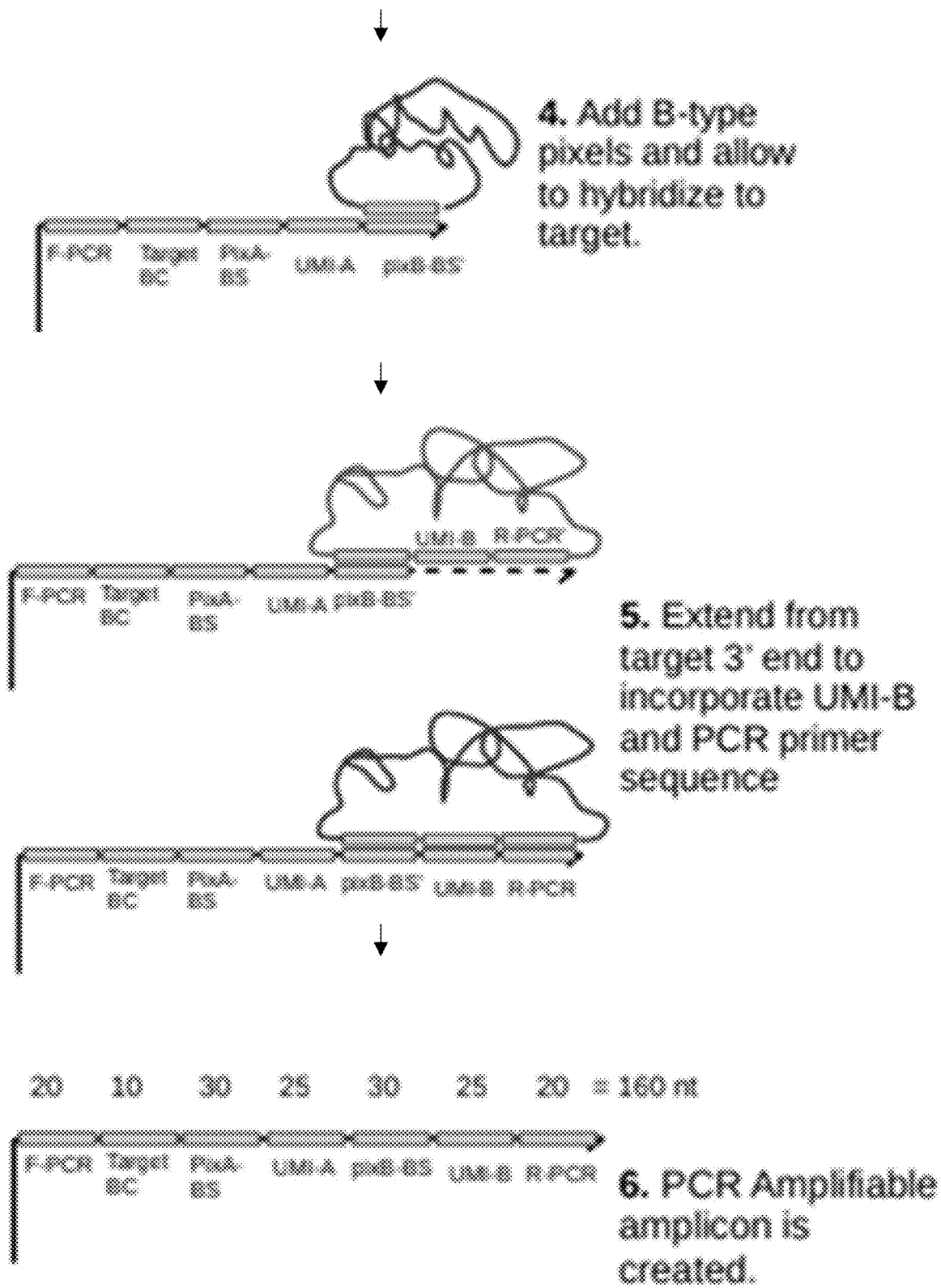
Figure 9C:
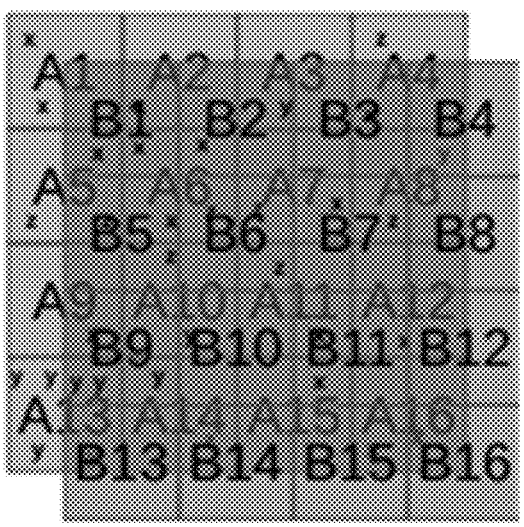

The steps of this method are laid out in detail in FIG. 9A-C. As can be seen from FIG. 9A-C, the primers may contain target identifier sequences, thereby allowing the assay to be multiplexed. In this method, a population of second primer extension products may be amplified and sequenced en masse. Each sequence read should contain a target identifier as well as two particle identifiers, one from the first set of particles and the other from the second set of particles. Because the sites to which the first and second sets of particles bind overlap in the separate hybridization reactions, the primers can be mapped to sites in the sample. Specifically, a relational map of the barcoded particles can be produced by figuring out which pairs of identifiers are added to a primer. The target sequences can be mapped onto the relational map, thereby providing a map of the binding sites of the primers (or the sites, e.g., the epitopes or sequences. to which they are bound).

Figure 10:
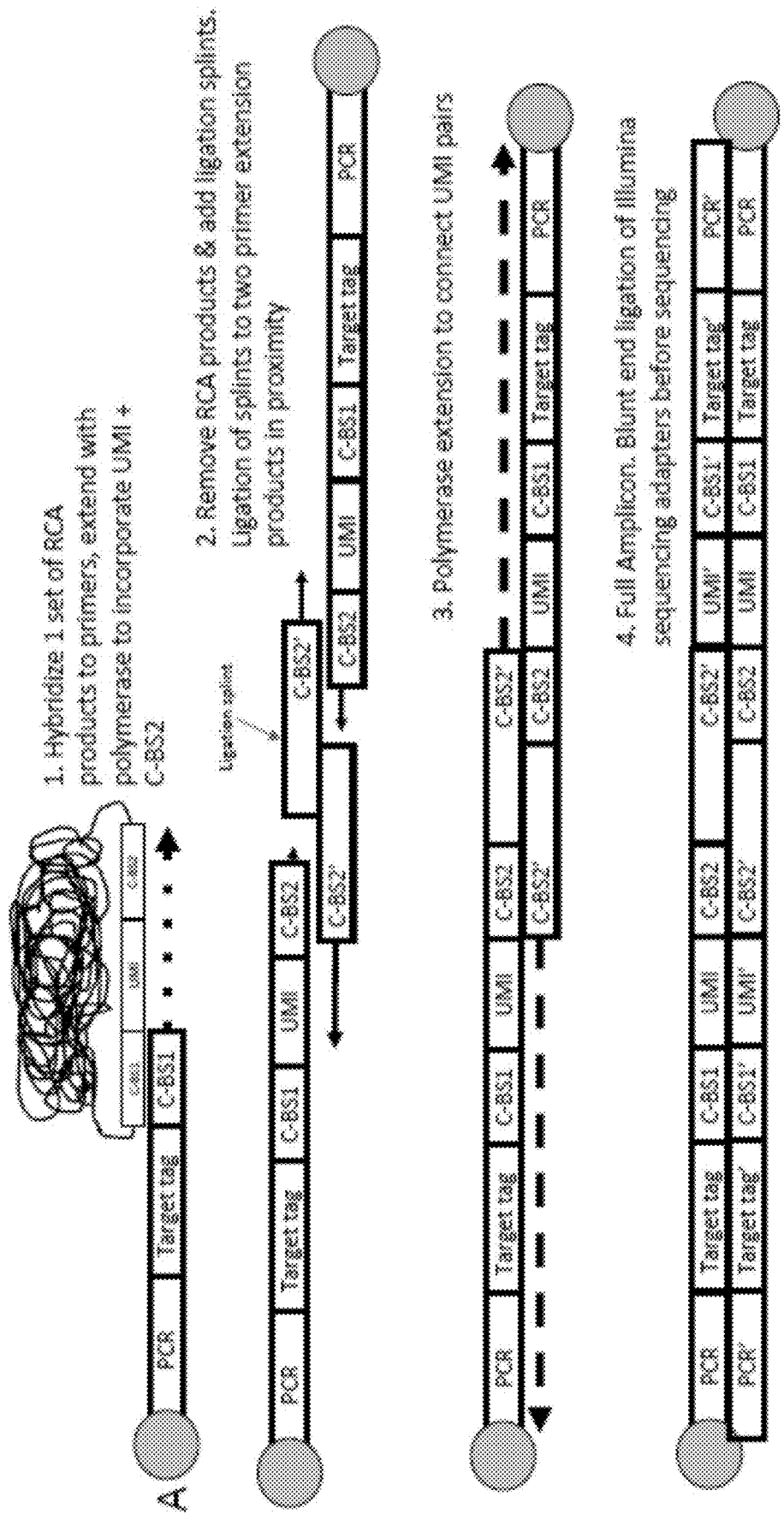
FIG. 10 schematically illustrates an alternative probe system and method of using the same.
Figure 11:
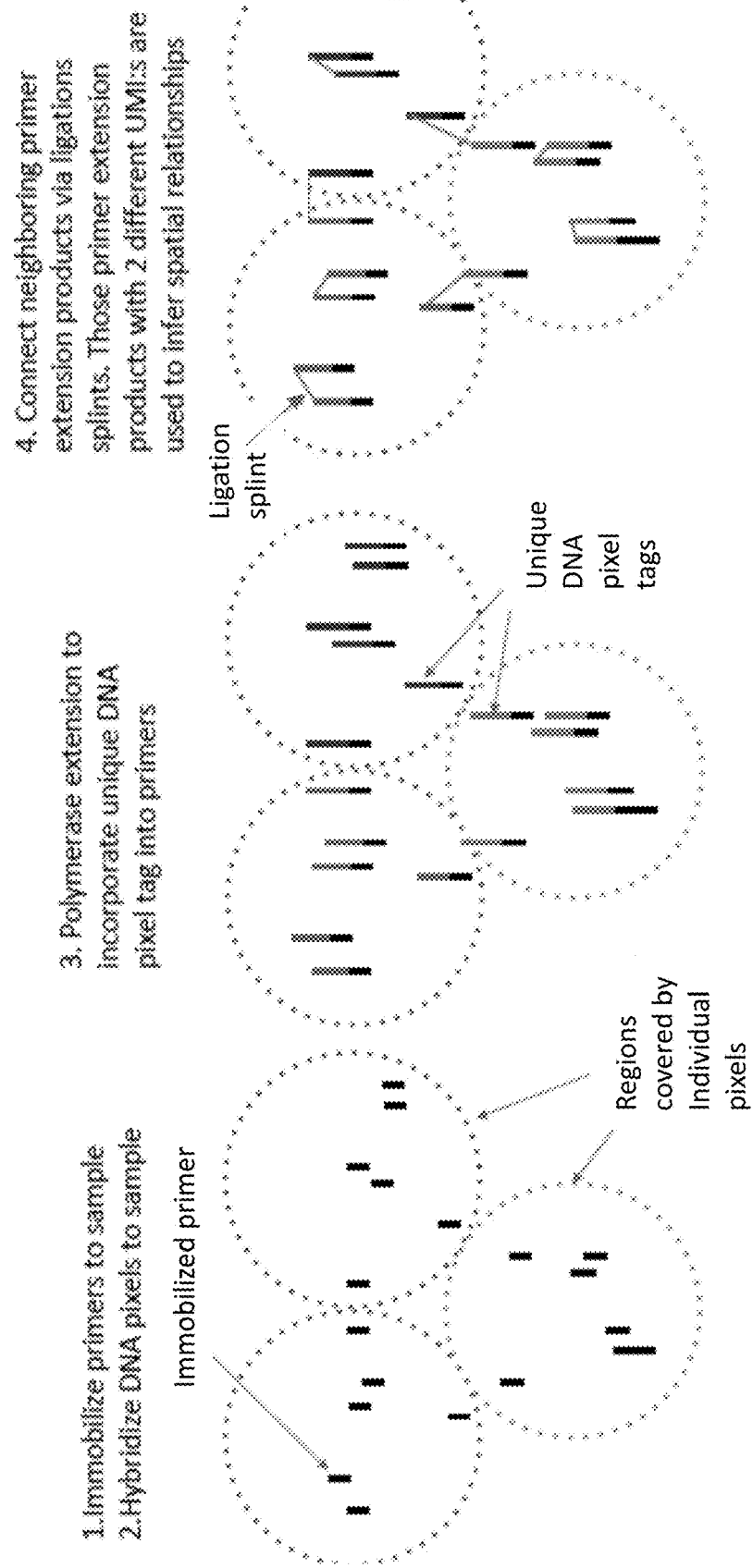
FIG. 11 schematically illustrates a method in which the alternative probe system shown in FIG. 10 can be used.

Alternative ligation-based embodiments are described below. These embodiments avoid the use of two sets of barcoded particles and, instead only 1 primer extension step is required. In these embodiments, the pairs of identifiers can be created by connecting nearby primer extension products via a ligation splint. These embodiments are schematically illustrated in FIGS. 10 and 11. In these embodiments, the probe system may comprise: a population of primer molecules (which, as shown, may contain a sequence that provides a primer binding site, a target identifier and primer sequence C-BS1); a set of barcoded particles that each have a nucleotide sequence comprising: (i) a primer binding sequence (C-BS1) that is complementary to the 3' end of the primer molecules, (ii) a unique particle identifier sequence (UMI), and (iii) a first template sequence (C-BS2). Instead of a second set of barcoded particles, this probe system comprises a ligation splint. As illustrated in FIG. 10, the ligation splint is composed of a first oligonucleotide and a second oligonucleotide, wherein the first oligonucleotide comprises a first sequence and the first template sequence (C-BST'); and the second oligonucleotide comprises a second sequence that is complementary to the first sequence, and the first template sequence (C-BST'). The two oligonucleotides in the splint may have the same sequence and hybridize to one another via sequences at the 5' ends.

In general terms, the components of this system are similar to the serial extension system components described above, except that the alternative system has a ligation splint instead of the second set of barcoded particles. For example, the barcoded particles may be rolling circle amplification (RCA) products, or the barcoded particles may be barcoded nanoparticles, wherein nucleotide sequence is tethered to the surface of the barcoded particles. Likewise, the primer molecules of (a) are synthetic oligonucleotides that are 10-200 nt in length, which may be linked to a binding agent, (e.g., an oligonucleotide probe, antibody, aptamer, etc). In some embodiments, the primer molecules may be cDNA molecules that have a primer sequence at the 3' end.

As with the serial extension embodiments, the set of barcoded particles may contain at least 10 particles, each having a unique particle identifier sequence. In this embodiment, the set of barcoded particles may each comprise at least 10 members (e.g., at least 100, at least 1,000, at least 10,000, at least 100,000, at least 1M at least 10 M, at least 100 M, at least 1B or at least 10B members), which are each uniquely identifiable by their particle identifier sequence. In some embodiments, the nucleic acid sequences of the barcoded particles may be identical to one another except for their particle identifier sequences.

The alternative probe system may be used to map binding events that are in or on a cellular sample in a similar way to the serial probe system described above. A method for adding unique particle identifier sequences to a primer using the alternative probe system is provided. This method, which is illustrated in FIGS. 10 and 11, may comprise hybridizing the set of barcoded particles with the population of primer molecules (which may be immobilized on a support, as shown), and extending the hybridized primer molecules using the nucleotide sequences as a template. This step results in the production of first primer extension products that contain i. the complement of a unique particle identifier sequence (UMI) from a barcoded particle and ii. the complement of the first template sequence (C-BS2). After the barcoded particles are removed, the method comprises hybridizing the first primer extension products with the ligation splint, wherein the complements of the first template sequence in two proximal first primer extension products hybridize to the first and second sequences of the ligation splint, as shown. Next, the method comprises ligating at least one of either the first and second oligonucleotides of the hybridized ligation splint to the first primer extension products and extending the 3' end of at least one of the first and second oligonucleotides in the splint using the first primer extension product in the ligation product as a template, thereby adding two unique particle identifier sequences to a primer. As illustrated in FIG. 10, the primers can be engineered to forward and reverse primer sequences and target identification sequences, thereby providing a product that contains PCR primer sites, a pair of target identification sequences and two particle identifiers. These sequences can be analyzed to determine the relative positions of the barcoded particles and primers (or the binding agents, probes or cDNA molecules to which they are tethered), as schematically illustrated in FIG. 11. As would be apparent, the method may comprise sequencing the second primer extension, thereby identifying which the pairs of unique particle identifier sequences are in the second primer extension products. The method may further comprise mapping the relative positions of the primers of i. using the pairs of unique particle identifier sequences that are in the second primer extension products.

As with the serial extension embodiments described above, the primers molecules may be attached to a cellular sample via a binding agent (e.g., an antibody, aptamer or probe), and the unique particle identifiers in the second primer extension products may indicate the relative position of the binding agents on the cellular sample. Likewise, the primers may be the 3' ends of cDNAs that are made in the cellular sample in situ, wherein the unique particle identifiers in the second primer extension products indicate the relative position of cDNAs in the cellular sample.

In any embodiment, barcoded particles may be mapped relative to one another if two complex identifiers are added to the same molecule. The map produced by the method may be a three-dimensional map or a two-dimensional map, depending on how the method is implemented. For example, if the complexes products are immobilized within cells (e.g., produced in situ in cells) then the map produced may be three dimensional. In other embodiments, e.g., if the complexes are immobilized on one or more surfaces (e.g., the surface of one or more cells that may be in suspension or mounted on a support), then the map produced by the method may be two dimensional or potentially three dimensional because, in theory, the map may be spherical. While the method can be applied to cells (as described below) the method can be adapted to map adjacent complexes that are immobilized on any surface, e.g., a glass slide that may have a tissue blot, or a western blot, etc. Likewise, although the complexes can be anchored to sites in or on cells or on a surface via an antibody (e.g., an antibody that is conjugated to an oligonucleotide that has a sequence that is complementary to a sequence in a complex), the complexes can be immobilized via any type of interaction, e.g., covalent or non-covalent interactions, directly or indirectly. For example, in some embodiments, the complexes may be bound to the cell via a binding agent (e.g., an aptamer, an antibody or an oligonucleotide, etc.), where the binding agent binds to a sequence in the complexes and a site in a cell or on the surface of the one or more cells. In some embodiments, the complexes may be immobilized via hybridization to an oligonucleotide that also hybridizes to a nucleic acid (e.g., to a cellular RNA) or the RCA products may be immobilized non-covalently to a site via electrostatic interactions, via a streptavidin/biotin interaction, or by a covalent linkage (e.g., via a click coupling).

In any embodiment, the complexes may be immobilized in or on cells that are in solution, cells that are on a support (e.g., a slide), cells that in a three-dimensional sample of tissue, or cells that are in a tissue section. A sample containing cells that are in solution may be a sample of cultured cells that have been grown as a cell suspension, for example. In other embodiments, disassociated cells (which cells may have been produced by disassociating cultured cells or cells that are in a solid tissue, e.g., a soft tissue such as liver of spleen, using trypsin or the like) may be used. In particular embodiments, the complexes may be immobilized on cells that can be found in blood, e.g., cells that in whole blood or a sub-population of cells thereof. Sub-populations of cells in whole blood include platelets, red blood cells (erythrocytes), and white blood cells (i.e., peripheral blood leukocytes, which are made up of neutrophils, lymphocytes, cosinophils, basophils and monocytes). These five types of white blood cells can be further divided into two groups, granulocytes (which are also known as polymorphonuclear leukocytes and include neutrophils, cosinophils and basophils) and mononuclear leukocytes (which include monocytes and lymphocytes). Lymphocytes can be further divided into T cells, B cells and NK cells. Peripheral blood cells are found in the circulating pool of blood and not sequestered within the lymphatic system, spleen, liver, or bone marrow. If cells that are immobilized on a support are used, then then the sample may be made by, e.g., growing cells on a planar surface, depositing cells on a planar surface, e.g., by centrifugation, by cutting a three dimensional object that contains cells into sections and mounting the sections onto a planar surface, i.e., producing a tissue section. In alternative embodiments, the surface may be made by absorbing cellular components onto a surface.

In any embodiment, the method may comprise immobilizing thousands, tens of thousands, hundreds of thousands or at least a million barcoded particles (each having a unique identifier), to a population of cells (e.g., via an antibody) so that on each cell the barcoded particles effectively coat the cell. The barcoded particles may hybridize to other oligonucleotides that are tethered to sites in or on a cell to produce a matrix comprising the barcoded particles. After hybridization, the unique identifier sequences of adjacent complexes can be copied from one barcoded particle to another. A physical map of the complexes, as well as the sites to which the barcoded particles bind to the cell, can be constructed based on the sequences that have been copied.

In addition to making a map of the barcoded particles, the method may involve performing a proximity assay between one or more binding agents that are bound to sites in the cells or on the surface of the cells (e.g., antibodies that are bound to cell surface markers on the cells). In these embodiments, a product may contain a pair of unique complex identifier sequences as well as a binding agent identifier sequence. In some embodiments, the binding agent may be an antibody-oligonucleotide conjugate and in other embodiments, the capture agent may be an oligonucleotide probe or cDNA. The oligonucleotide and the capture agent may be linked via a number of different methods, including those that use maleimide or halogen-containing groups, which are cysteine-reactive. The capture agent and the oligonucleotide may be linked proximal to or at the 5' end of the oligonucleotide, proximal to or at the 3' end of the oligonucleotide, or anywhere in-between. In some embodiments, the oligonucleotides may be linked to the capture agents by a linker that spaces the oligonucleotide from the capture agents. Oligonucleotides may be linked to capture agents using any convenient method, as described above. In many embodiments, the sequence of an oligonucleotide that is conjugated to a binding agent uniquely identifies the epitope or sequence to which the binding agent binds. For example, if the method is performed using 10 different antibodies, then each antibody is tethered to a different sequence that identifies the epitope to which the antibody binds. This feature allows the method to be multiplexed and, in some embodiments, at least 5, at least 10, at least 20 or at least 50 different antibodies that bind to different markers in or on the surface of a cell can be used in the method. Each antibody is conjugated to a different antibody identifier sequence, and the antibody identifier sequences allow the binding events for a particular antibody to be mapped. Such tagged antibodies are described in, e.g., Wu et al (Nat. Comm. 2019 10:3854) and U.S. Pat. No. 20160281134, and others.

EMBODIMENTS

Embodiment 1. A probe system comprising: (a) a population of primer molecules; (b)

a first set of barcoded particles that each have a nucleotide sequence comprising: (i) a primer binding sequence that is complementary to the 3' end of the primer molecules of (a), (ii) a unique particle identifier sequence, and (iii) a first template sequence; (c) a second set of barcoded particles that each have a nucleotide sequence comprising: (i) the first template sequence, and (ii) a unique particle identifier sequence; wherein extension of the primer molecules of (a) using the first set of barcoded particles of (b) as a template produces primer extension products that contain the complement of a unique particle identifier sequence of a particle of (b) (ii) and the complement of the first template sequence.

Embodiment 2. The probe system of embodiment 1, wherein the barcoded particles of (b) and/or (c) are rolling circle amplification (RCA) products.

Embodiment 3. The probe system of embodiment 1, wherein the barcoded particles of (b) and/or (c) are barcoded nanoparticles, wherein the nucleotide sequences are tethered to the surface of the barcoded particles.

Embodiment 4. The probe system of any prior embodiment, wherein primer molecules of (a) are synthetic oligonucleotides that are 10-200 nt in length.

Embodiment 5. The probe system of any prior embodiment, wherein the primer molecules of (a) are cDNA molecules that have a primer sequence at the 3' end.

Embodiment 6. The probe system of any prior embodiment, wherein the primer molecules of (a) have a forward primer sequence and the nucleotide sequence of the second set of barcoded particles has a reverse primer sequence downstream of the unique particle identifier sequence.

Embodiment 7. The probe system of any prior embodiment, wherein the primer molecules of (a) are linked to a binding agent, (e.g., an oligonucleotide probe, antibody, aptamer, etc).

Embodiment 8. The probe system of embodiment 7, wherein the primer molecules further comprise target identifier sequences that indicate the binding agent to which they are linked.

Embodiment 9. The probe system of any of embodiments 1-6, wherein the primer molecules are linked to a planar substrate.

Embodiment 10. The probe system of any prior embodiment, wherein the first and second sets of barcoded particles independently contain at least 10,000 particles, each having a unique particle identifier sequence.

Embodiment 11. The probe system of any prior embodiment, wherein the nucleotide sequence of the second set of barcoded particles lacks the primer binding sequence of (b) (i).

Embodiment 12. A method for adding unique particle identifier sequences to a primer using the probe system of any of embodiments 1-11, comprising;
  i. hybridizing the first set of barcoded particles of (b) with the population of primer molecules of (a),
  ii. extending the hybridized primer molecules using the nucleotide sequence of the first set of barcoded particles as a template to produce first primer extension products that contain i. the complement of a unique particle identifier sequence from a barcoded particle in the first set of barcoded particles and ii. the complement of the first template sequence;
  iii. removing the first set of barcoded particles;
  iv. hybridizing the first primer extension products with the second set of barcoded particles, wherein the complement of the first template sequence in the first primer extension products hybridizes to the first template sequence in the second set of barcoded particles; and
  v. extending the first primer extension products using the nucleotide sequence of the second set of barcoded particles as a template to produce second primer extension products that contain:
    a unique particle identifier sequence from a barcoded particle in the first set of barcoded particles,
    the first template sequence, and
    a unique particle identifier sequence from a barcoded particle in the second set of barcoded particles.

Embodiment 13. The method of embodiment 12, wherein the primer molecules have a forward primer sequence and the nucleotide sequence of the second set of barcoded particles has a reverse primer sequence downstream of the unique particle identifier sequence, and the method comprises amplifying the second primer extension products of v.

Embodiment 14. The method of embodiment 12 or 13, where the method comprises sequencing the second primer extension products of v.

Embodiment 15. The method of embodiment 14, mapping the relative positions of the primers of i. using the pairs of unique particle identifier sequences that are in the second primer extension products.

Embodiment 16. The method of any of embodiments 12-15, wherein the primers are attached to a planar substrate, and the method results in an array of the second primer extension products on the substrate.

Embodiment 17. The method of any of embodiments 12-15, wherein the primers are attached to a cellular sample via a binding agent, and the unique particle identifiers in the second primer extension products indicate the relative position of the binding agents on the cellular sample.

Embodiment 18. The method of any of embodiments 12-15, wherein the primers are cDNAs that are made in the cellular sample in situ, wherein the unique particle identifiers in the second primer extension products indicate the relative position of cDNAs in the cellular sample.

Embodiment 19. A method for making a map of binding events in or on a cellular sample, comprising: (a) obtaining: i. a sample containing primer molecules that are bound to sites in or on cells; ii. a first set of barcoded particles that each have a nucleotide sequence comprising: (i) a primer binding sequence that is complementary to the 3' end of the primer molecules of (a), (ii) a unique particle identifier sequence, and (iii) a first template sequence; iii. a second set of barcoded particles that each have a nucleotide sequence comprising: (i) the first template sequence, and (ii) a unique particle identifier sequence; (b) specifically hybridizing the first set of barcoded particles of (a) (ii) with the sample, wherein the nucleotide sequence of at least some of the first set of barcoded particles hybridizes to at least two primer molecules; (c) extending the primers that are hybridized to barcoded particles in step (b) using the nucleotide sequences to which the primers are hybridized as a template to produce first primer extension products that each comprise a first unique particle identifier sequence; (d) removing the first set of barcoded particles from the sample; (e) specifically hybridizing the second set of barcoded particles of (a) (iii) with the first primer extension products of (c), wherein the nucleotide sequences of at least some of the second set of barcoded particles hybridizes to at least two molecules of the primer extension products; (f) extending the first primer extension products that are hybridized to a barcoded particle in step (e) using the nucleotide sequences to which the primers are hybridized as a template to produce second primer extension products that comprise the two unique particle identifier sequences; (g) determining which unique particle identifier sequence or complements thereof are in second primer extension products; and (h) making a map of the relative positions of the primers of (a)(i) using the unique particle identifier sequences that are in the second primer extension products.

Embodiment 20. The method of embodiment 19, wherein the sample of (a) is made by binding primers that are attached to binding agents to sites that are in or on the cells.

Embodiment 21. The method of embodiment 20, wherein the binding agents are oligonucleotide probes, antibodies or aptamers.

Embodiment 22. The method of embodiment 20 or 21, wherein the primers further comprise target identifier sequences that indicate the binding agent to which they are linked.

Embodiment 23. The method of embodiment 19, wherein the sample of (a) is made by hybridizing a first primer to RNA in the cell, extending the primer to make cDNA, and appending a second primer onto the 5' end of the cDNA.

Embodiment 24. The probe system of any prior embodiment, wherein the nucleotide sequence of the second set of barcoded particles lacks the primer binding sequence of the first set of barcoded particles.

Embodiment 25. A probe system comprising: (a) a population of primer molecules; (b) a set of barcoded particles that each have a nucleotide sequence comprising: (i) a primer binding sequence that is complementary to the 3' end of the primer molecules of (a), (ii) a unique particle identifier sequence, and (iii) a first template sequence; and (c) a ligation splint comprising a first oligonucleotide and a second oligonucleotide, wherein the first oligonucleotide comprises a first sequence and the first template sequence; and the second oligonucleotide comprises a second sequence that is complementary to the first sequence, and the first template sequence.

Embodiment 26. The probe system of embodiment 25, wherein the barcoded particles of (b) are rolling circle amplification (RCA) products.

Embodiment 27. The probe system of embodiment 25, wherein the barcoded particles of (b) are barcoded nanoparticles, wherein nucleotide sequence of (b) is tethered to the surface of the barcoded particles.

Embodiment 28. The probe system of any of embodiments 25-27, wherein primer molecules of (a) are synthetic oligonucleotides that are 10-200 nt in length.

Embodiment 29. The probe system of any of embodiments 25-27, wherein the primer molecules of (a) are cDNA molecules that have a primer sequence at the 3' end.

Embodiment 30. The probe system of any of embodiments 25-28, wherein the primer molecules of (a) are linked to a binding agent, (e.g., an oligonucleotide probe, antibody, aptamer, etc).

Embodiment 31. The probe system of any of embodiments 25-30, wherein the set of barcoded particles may contain at least 10,000 particles, each having a unique particle identifier sequence.

Embodiment 32. A method for adding unique particle identifier sequences to a primer using the probe system of any of embodiments 25-31, comprising;
  i. hybridizing the set of barcoded particles of (b) with the population of primer molecules of (a),
  ii. extending the hybridized primer molecules using the nucleotide sequences as a template to produce first primer extension products that contain i. the complement of a unique particle identifier sequence from a barcoded particle and ii. the complement of the first template sequence;
  iii. removing the barcoded particles;
  iv. hybridizing the first primer extension products with the ligation splint, wherein the complements of the first template sequence in two proximal first primer extension products hybridize to the first and second sequences of the ligation splint;
  v. ligating at least one of the first or the second oligonucleotide of the hybridized ligation splint to the first primer extension products and extending the 3' end of the ligated first or second oligonucleotide in the splint using the first primer extension product in the ligation product as a template, thereby adding two unique particle identifier sequences to a primer.

Embodiment 33. The method of embodiment 32, where the method comprises sequencing the second primer extension products of v.

Embodiment 34. The method of embodiment 32 or 33, further comprising mapping the relative positions of the primers of i. using the pairs of unique particle identifier sequences that are in the second primer extension products.

Embodiment 35. The method of any of embodiments 32-34, wherein the primers molecules of i. are attached to a cellular sample via a binding agent, and the unique particle identifiers in the second primer extension products indicate the relative position of the binding agents on the cellular sample.

Embodiment 36. The method of any of embodiments 32-34, wherein the primers are cDNAs that are made in the cellular sample in situ, wherein the unique particle identifiers in the second primer extension products indicate the relative position of cDNAs in the cellular sample.

EXAMPLES

The following examples are put forth so as to provide those of ordinary skill in the art with additional disclosure and description of how to make and use the present invention, and are not intended to limit the scope of what the inventors regard as their invention nor are they intended to represent that the experiments below are all or the only experiments performed.

Methods

Probe circularization and Rolling circle amplification: Probe oligo (1 or 2) was circularized using template oligo (3 or 4) in 50 μl ligation reactions containing 100 nM probe oligo, 100 nM template oligo, 1 mM ATP, 200 U T4 DNA ligase and a reaction buffer containing 33 mM Tris-acetate, 10 mM Mg-acetate, 66 mM K-acetate, 1 mM DTT and 0.1% Tween20. The reaction was incubated at 37° C. for 30 minutes.

Non-circularized probes were digested by adding 10 U Exonuclease I and 100 U exonuclease III to each reaction following ligation. The exonuclease digestion was performed for 30 min at 37° C., followed by heat inactivation at 85° C. for 20 min.

RCA primer oligo 3 or 4 was added to each reaction after exonuclease digestion to a concentration of 100 nM and was allowed to hybridize to the circularized probes by incubation at 37° C. for 20 min.

Rolling circle amplification was performed in 75 μl reactions containing 2.5 nM circularized probe, 0.75 mM of each d(AUGC) TP and 7.5 U phi29 DNA polymerase, in the same reaction buffer as used for probe circularization. The reaction was incubated for 20 min at 37° C., followed by heat inactivation at 65° C. for 10 min.

Cell staining and fixation: Raji and Jurkat cells were aspirated from separate T75 flasks and spun down at 300×g for 5 min. Cells were counted and cell suspension corresponding to 1 M cells were taken. Cells were washed twice in FACS buffer (2% FBS, 2 mM EDTA in 1×PBS). Cells were blocked with Fc blocking agent and spun down to remove the supernatant. A pool of 2 TotalSeq B (Biolegend inc) antibody-oligonucleotide conjugates (oligo 8-27) targeting various immune cell markers (CD3, CD4, etc) at a concentration of 5 µg/ml of each conjugate was added to the cells and incubated for 30 min on ice. The conjugate stained cells were washed twice with 300 µl FACS buffer after which the cells were spun down, supernatant removed and 250 µl of 1% PFA was added to fix the sample. After 10 minute incubation at RT, the fixation was quenched by addition of 12.5 µl of 2.5 M Glycine, followed by a wash with 250 µl of 125 mM Glycine in PBS. After another wash in PBS cells were resuspended in PBS and stored at +4° C. until use.

Primer extension assay: Conjugate-stained and fixated Raji and Jurkat cells were mixed at a 1:1 ratio and an aliquot corresponding to approximately 20 000 cells in total was put in a PCR tube.

Hybridization of RCA products to antibody-conjugate oligos bound to cells were performed in a 40 µl reaction containing 2.5 nM RCA products (originating from oligo 1), 0.5 µM of blocking oligo (5), in a buffer with 300 mM NaCl, 15 mM MgCl$_2$, 20 mM Tris-HCl (pH 8). The reaction was incubated for 15 minutes at 55° C.

The sample were centrifuged at 500×g for 2 min to pellet the cells, supernatant removed and 100 µl of a wash buffer (50 mM NaCl, 1 mM EDTA, 20 mM Tris-HC, pH 81) was added and cells resuspended. The sample was again centrifuged to pellet cells and supernatant removed.

A 50 µl DNA polymerase extension reaction was performed to incorporate pixel barcode sequence by adding a mastermix containing 0.2 mM dNTPs, 1 µl of Klentaq DNA polymerase in a buffer comprising 50 mM Na-acetate, 10 mM Mg-acetate, 20 mM Tris-acetate, 100 µg/ml BSA. The reaction was incubated for 15 min at 30 C. A washing step was again performed under the same conditions as previously described after which a USER digestion (Uracil DNA glycosylase+Endonuclease VII) reaction was performed to degrade DNA pixels by adding 50 µl of a buffer comprising 50 mM NaCl, 1 mM EDTA, 20 mM Tris-HC and 1 U of USER enzyme. The reaction was incubated for 30 min at 37° C.

A wash step was performed before adding a 50 µl USER inactivation mastermix consisting of 1 U UGI protein in 50 mM NaCl, 1 mM EDTA, 20 mM Tris-HCl, pH 8. The reaction was incubated for 15 min at 37° C.

After a wash step a second RCA product hybridization reaction was performed, using RCA products originating from oligo 2, using otherwise the same conditions as previously described for hybridization of RCA product 1. Similarly, the same protocols for extension and USER inactivation were performed following the 2nd hybridization reaction. Following the 2nd USER digestion step, a washing step was performed before resuspending the cells in 50 µl of wash buffer. The resulting cell suspension was quantified and diluted to a concentration of 20 cells/µl.

After the serial extension assay, each conjugate oligonucleotide bound to cells via antibody-binding had two DNA pixel barcode sequences and a reverse PCR primer motif incorporated through the extension steps of the assay.

PCR was performed for 15 cycles in a reaction containing 5 µl of diluted sample, 0.2 mM dNTPs, 0.4 µM each of fwd and rev primers containing Illumina adapter sequences (6, 7), 1 µl of Phusion DNA polymerase, in 1× of Phusion HF reaction buffer. The PCR reaction consisted of: 98° C. denaturation for 1 min, followed by 15 cycles of 10 s denaturation at 98° C., 30 s annealing at 60°° C., 40 s at 72° C. before a final extension at 72° C. for 5 min.

The PCR product was finally purified using Ampure XP beads following the manufacturer's instructions, but using a bead-to-sample ratio of 1.2. The purified PCR product was quantified using a Qubit fluorometer and sequenced on an Illumina NextSeq 2000 sequencer.

| SEQ ID NO | name | seq |
|---|---|---|
| 1 | D12_PLA | GCTTTAAGGCCGGTCCTAGCAANNNNNNNNN NNNNNNNNNNNNNCAACATCAGTATTCCCAG GCTACCTGCAGGTTAAGCGGATTG |
| 2 | D15_PL-B | CAACATCAGTATTCCCAGGCTAAAANNNNNN NNNNNNNNNNNNNNNAGATCGGAAGAGCGT CGTGTAGGGAAAGACCTGCAGGTTAAGCGG ATTG |
| 3 | D12_PLT_A | TTGCTAGGACCGGCCTTAAAGCCAATCCGC TTAACCTGCAGG |
| 4 | D14-PLTB | TAGCCTGGGAATACTGATGTTGCAATCCGC TTAACCTGCAGG |
| 5 | D2_blocker | CCTGCAGGTTAAGCGGATTGmUmUmUmUmU |
| 6 | Fwd primer | CAAGCAGAAGACGGCATACGAGATCGAGTA ATGTGACTGGAGTTCAGAC*G*T*G |
| 7 | Rev primer | AATGATACGGCGACCACCGAGATCTACACT ATAGCCTACACTCTTTCCCTACACGACG*C *T*C |
| 8 | CD45_TSeqB | GTGACTGGAGTTCAGACGTGTGCTCTTCCG ATCTNNNNNNNNNNNTCCCTTGCGATTTACN NNNNNNNNNGCTTTAAGGCCGGTCCTAGC*A *A |
| 9 | CD3_TSeqB | GTGACTGGAGTTCAGACGTGTGCTCTTCCG ATCTNNNNNNNNNNNTATCCCTTGGGATGGN NNNNNNNNNGCTTTAAGGCCGGTCCTAGC*A *A |
| 10 | CD19_TSeqB | GTGACTGGAGTTCAGACGTGTGCTCTTCCG ATCTNNNNNNNNNNNCTGGGCAATTACTCGN NNNNNNNNNGCTTTAAGGCCGGTCCTAGC*A *A |
| 11 | IgG1ctrl_TSeqB | GTGACTGGAGTTCAGACGTGTGCTCTTCCG ATCTNNNNNNNNNNNGCCGGACGACATTAAN NNNNNNNNNGCTTTAAGGCCGGTCCTAGC*A *A |
| 12 | CD20_TSeqB | GTGACTGGAGTTCAGACGTGTGCTCTTCCG ATCTNNNNNNNNNNNTTCTGGGTCCCTAGAN NNNNNNNNNGCTTTAAGGCCGGTCCTAGC*A *A |
| 13 | CD69_TSeqB | GTGACTGGAGTTCAGACGTGTGCTCTTCCG ATCTNNNNNNNNNNNGTCTCTTGGCTTAAAN NNNNNNNNNGCTTTAAGGCCGGTCCTAGC*A *A |
| 14 | HLA-DR_TSeqB | GTGACTGGAGTTCAGACGTGTGCTCTTCCG ATCTNNNNNNNNNNNAATAGCGAGCAAGTAN NNNNNNNNNGCTTTAAGGCCGGTCCTAGC*A *A |
| 15 | CD8_TSB | GTGACTGGAGTTCAGACGTGTGCTCTTCCG ATCTNNNNNNNNNNNGCTGCGCTTTCCATTN NNNNNNNNNGCTTTAAGGCCGGTCCTAGC*A *A |

-continued

| SEQ ID NO | name | seq |
|---|---|---|
| 16 | CD14_TSB | GTGACTGGAGTTCAGACGTGTGCTCTTCCG ATCTNNNNNNNNNNNCAATCAGACCTATGAN NNNNNNNNGCTTTAAGGCCGGTCCTAGC*A *A |
| 17 | IgG2isoCtrl_TSB | GTGACTGGAGTTCAGACGTGTGCTCTTCCG ATCTNNNNNNNNNNNATATGTATCACGCGAN NNNNNNNNGCTTTAAGGCCGGTCCTAGC*A *A |
| 18 | CD45RA_TSB | GTGACTGGAGTTCAGACGTGTGCTCTTCCG ATCTNNNNNNNNNNNTCAATCCTTCCGCTTN NNNNNNNNGCTTTAAGGCCGGTCCTAGC*A *A |
| 19 | CD45RO_TSB | GTGACTGGAGTTCAGACGTGTGCTCTTCCG ATCTNNNNNNNNNNNCTCCGAATCATGTTGN NNNNNNNNGCTTTAAGGCCGGTCCTAGC*A *A |
| 20 | CD62L_TSB | GTGACTGGAGTTCAGACGTGTGCTCTTCCG ATCTNNNNNNNNNNNGTCCCTGCAACTTGAN NNNNNNNNGCTTTAAGGCCGGTCCTAGC*A *A |
| 21 | CD82_TSB | GTGACTGGAGTTCAGACGTGTGCTCTTCCG ATCTNNNNNNNNNNNTCCCACTTCCGCTTTN NNNNNNNNGCTTTAAGGCCGGTCCTAGC*A *A |
| 22 | CD7_TSB | GTGACTGGAGTTCAGACGTGTGCTCTTCCG ATCTNNNNNNNNNNNTGGATTCCCGGACTTN NNNNNNNNGCTTTAAGGCCGGTCCTAGC*A *A |
| 23 | CD70_TSB | GTGACTGGAGTTCAGACGTGTGCTCTTCCG ATCTNNNNNNNNNNNCGCGAACATAAGAAGN NNNNNNNNGCTTTAAGGCCGGTCCTAGC*A *A |
| 24 | CD72_TSB | GTGACTGGAGTTCAGACGTGTGCTCTTCCG ATCTNNNNNNNNNNNCAGTCGTGGTAGATAN NNNNNNNNGCTTTAAGGCCGGTCCTAGC*A *A |
| 25 | CD162_TSB | GTGACTGGAGTTCAGACGTGTGCTCTTCCG ATCTNNNNNNNNNNNATATGTCAGAGCACCN NNNNNNNNGCTTTAAGGCCGGTCCTAGC*A *A |
| 26 | CD26_TSB | GTGACTGGAGTTCAGACGTGTGCTCTTCCG ATCTNNNNNNNNNNNGGTGGCTAGATAATGN NNNNNNNNGCTTTAAGGCCGGTCCTAGC*A *A |
| 27 | CD63_TSB | GTGACTGGAGTTCAGACGTGTGCTCTTCCG ATCTNNNNNNNNNNNGAGATGTCTGCAACTN NNNNNNNNGCTTTAAGGCCGGTCCTAGC*A *A |

Results

The combination of 2 DNA pixel barcodes incorporated onto each conjugate oligo represents two DNA pixels that were in proximity to the molecule during the serial extension assay since each pixel only occupies a distinct region of space. This, together with the fact that multiple neighboring molecules will thus share the same pixel barcode allows for a spatial reconstruction of relative positions of each molecule, using a graph theory approach by considering the DNA pixel barcodes as nodes in a graph and the combination of 2 pixel barcodes of each molecule represents an edge (link) in the graph.

A series of data filtering steps were performed on the 40 million reads generated. In short, the filtering steps consisted of removal of reads that were shorter than the expected length, did not contain common sequence motifs expected at certain positions, and only observed once in the data. The average read depth was 7.99 i.e., on average there were 7.99 copies of each unique molecule.

Of the reads remaining after filtering, a total of 3.4 M unique molecules were identified based on a unique molecular identifier (UMI) sequence that was part of the conjugation oligo sequence. A total of 361575 DNA pixel sequences from set A and 451177 DNA pixel sequences from set B were found. The average number of unique conjugate oligos associated with each pixel from set A was 7.47 and 9.31 for pixel set B.

Figure 18A:
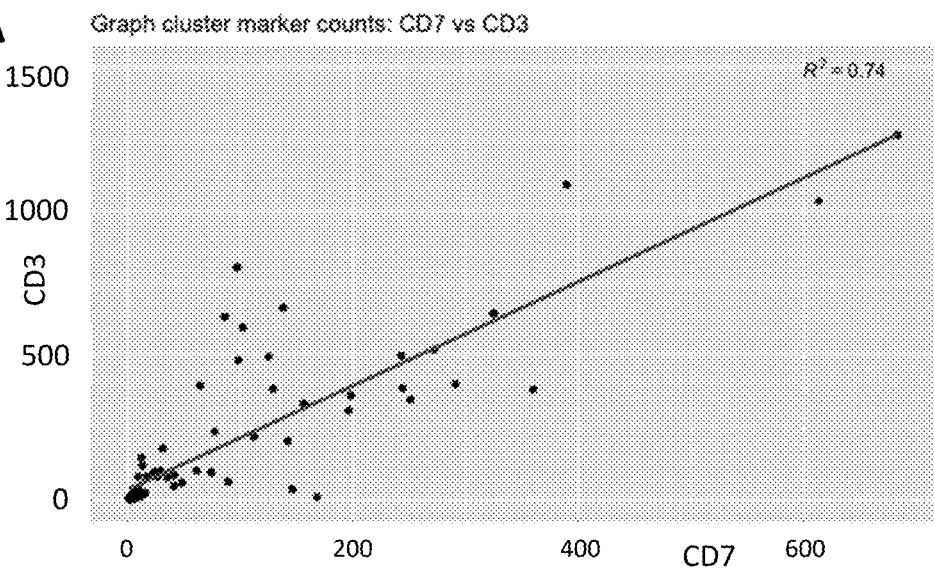
FIGS. 18A-18C show correlation plots of marker counts within each cluster. Poor correlation between CD3 and HLA-DR suggests each cluster represents a single cell.
Figure 18B:
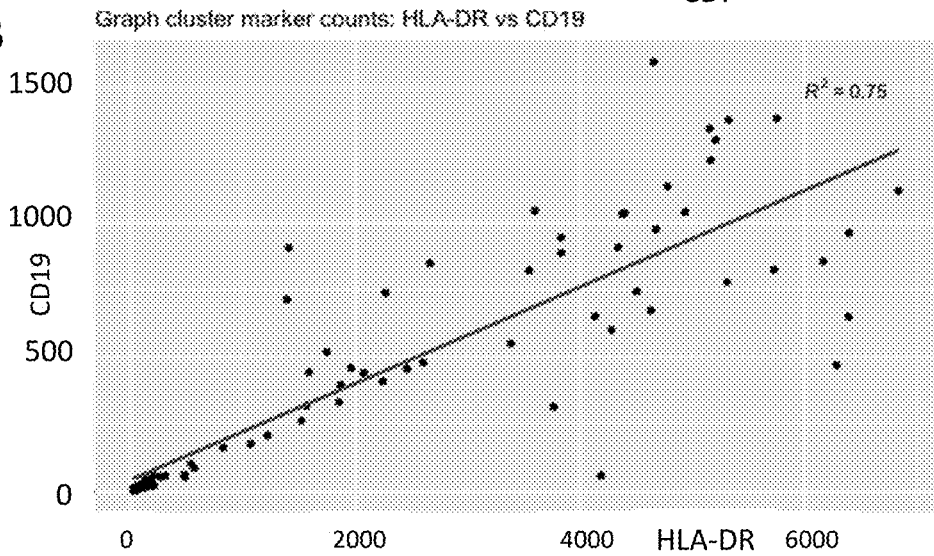
Figure 18C:
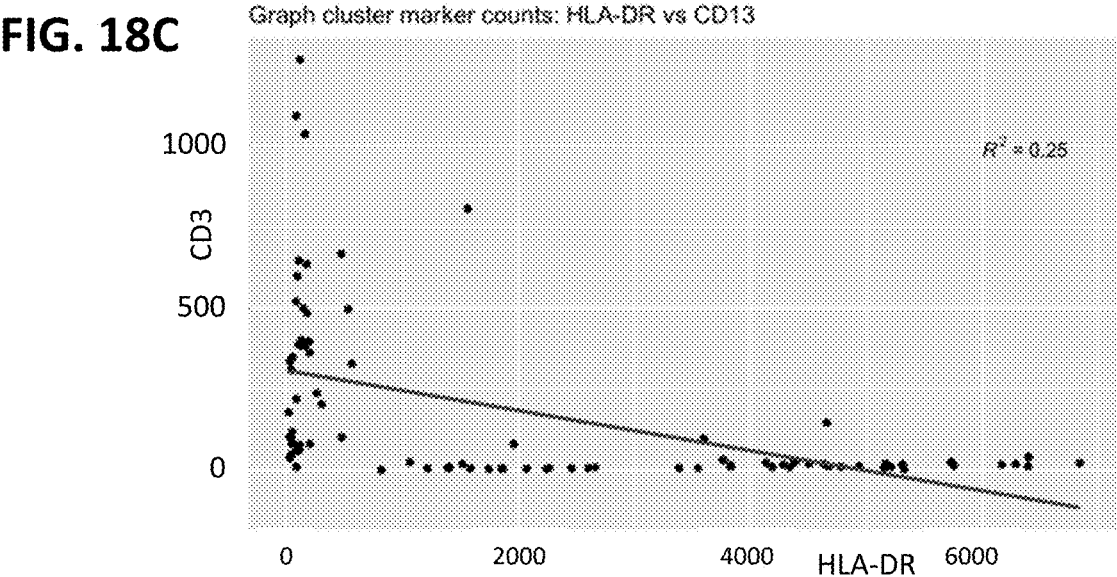

After filtering away small graph components, the generated graph, or physical map, consisted of a set of approximately 100 graph components (clusters), each composing at least 1000 nodes. An induced subgraph was generated for each of the components and the count of each surface marker type was summarized for each cluster. The correlation of marker counts within each cluster was compared using scatter plots (FIGS. 18A-18C). A linear correlation in marker counts was observed if plotting two B-cell markers against each other (HLA-DR, CD19) or two T-cell markers (CD3, CD7). No such correlation was observed if instead plotting a B-cell marker (HLA-DR) against a T-cell marker (CD3). Together, these results show that each separate graph cluster was generated from and represent a single cell in this experiment that contained a sample with a mixture of B and T-cells, Raji and Jurkat.

Figure 19:
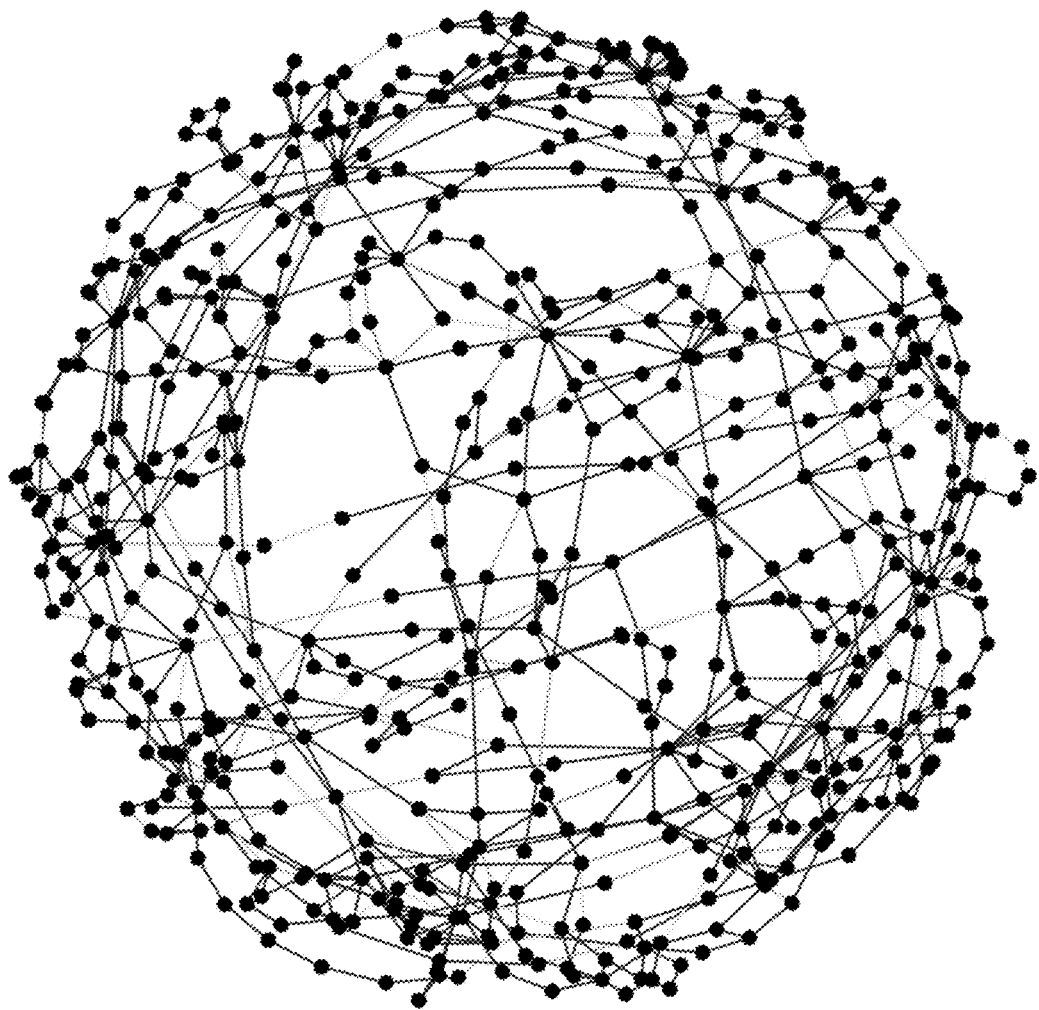
FIG. 19 is a visualization of a graph component (cluster) using a force-generated layout algorithm. Different antibody types can be distinguished.

A representative cluster was selected and visualized using the Kamada-Kawai force-generated graph layout algorithm (FIG. 19). Each edge (link) of the graph in FIG. 19 can be represented in a different color which identifies the different antibody types, where the information has been decoded from the barcode sequence of each the oligonucleotides conjugated to an antibody, and each node of the graph represents a DNA pixel sequence.

What is claimed is:

1. A probe system comprising:
   (a) a population of nucleic acid molecules that have an extendible 5' end or an extendible 3' end;
   (b) a set of barcoded particles that each have a nucleotide sequence comprising:
      (i) a binding sequence that is complementary to the extendible end of the nucleic acid molecules of (a),
      (ii) a unique particle identifier sequence, and
      (iii) a first template sequence; and
   (c) a ligation splint comprising a first oligonucleotide and a second oligonucleotide, wherein:
      the first oligonucleotide comprises a first sequence and the first template sequence; and
      the second oligonucleotide comprises a second sequence that is complementary to the first sequence, and the first template sequence, whereby the first oligonucleotide and the second oligonucleotide hybridize with one another via the respective first and second sequences, wherein:
      the first template sequence of the ligation splint is 3' of the first and second sequences of the first and second oligonucleotides if the population of nucleic acid molecules has an extendible 3' end, and
      the first template sequence of the ligation splint is 5' of the first and second sequences of the first and second oligonucleotides if the population of nucleic acid molecules has an extendible 5' end.

2. The probe system of claim 1, wherein the barcoded particles of (b) are rolling circle amplification (RCA) products.

3. The probe system of claim 1, wherein the barcoded particles of (b) are barcoded nanoparticles, wherein the nucleotide sequence of (b) is tethered to the surface of the barcoded particles.

4. The probe system of claim 1, wherein nucleic acid molecules of (a) are synthetic oligonucleotides that are 10-200 nt in length.

5. The probe system of claim 1, wherein the nucleic acid molecules of (a) are cDNA molecules.

6. The probe system of claim 1, wherein the nucleic acid molecules of (a) are linked to a binding agent.

7. The probe system of claim 1, wherein the set of barcoded particles may contains at least 10,000 particles, each having a unique particle identifier sequence.

8. A method for adding unique particle identifier sequences to a nucleic acid using a probe system as claimed in any preceding claim, comprising;
   (i) hybridizing the set of barcoded particles of (b) with the population of nucleic acid molecules of (a),
   (ii) extending the hybridized nucleic acid molecules using the nucleotide sequences as a template to produce first extension products that contain i. the complement of a unique particle identifier sequence from a barcoded particle and ii. the complement of the first template sequence wherein the extending is done by primer extension if the nucleic acid molecules have an extendible 3' end or gap-fill ligation if the nucleic acid molecules have an extendible 5' end;
   (iii) removing the barcoded particles;
   (iv) hybridizing the first extension products with the ligation splint, wherein the complements of the first template sequence in two proximal first extension products hybridize to the first and second template sequences of the ligation splint;
   (v) ligating at least one of the first or the second oligonucleotides of the hybridized ligation splint to the first extension products and extending the 3' end or the 5' end of the ligated first or second oligonucleotide in the splint using the first extension product in the ligation product as a template, thereby adding two unique particle identifier sequences to a nucleic acid, wherein the extending is done by primer extension if the 3' end is extended or gap-fill ligation if the 5' end is extended.

9. The method of claim 8, where the method comprises sequencing the products of (v).

10. The method of claim 8, further comprising mapping the relative positions of the nucleic acid molecules of (i) using the pairs of unique particle identifier sequences that are in the products of (v).

11. The method of claim 8, wherein the nucleic acid molecules of (i) are attached to a cellular sample via a binding agent, and the unique particle identifiers in products of (v) indicate the relative position of the binding agents on the cellular sample.

12. The method of claim 8, wherein the nucleic acid molecules are cDNAs that are made in a cellular sample in situ, wherein the unique particle identifiers in the products of (v) indicate the relative position of cDNAs in the cellular sample.

* * * * *

SEQUENCE LISTING

```
Sequence total quantity: 27
SEQ ID NO: 1         moltype = DNA  length = 84
FEATURE              Location/Qualifiers
misc_feature         1..84
                     note = synthetic sequence
misc_difference      23..42
                     note = n is a, c, g, or t
source               1..84
                     mol_type = other DNA
```

```
                          organism = synthetic construct
SEQUENCE: 1
gctttaaggc cggtcctagc aannnnnnnn nnnnnnnnnn nncaacatca gtattcccag    60
gctacctgca ggttaagcgg attg                                           84

SEQ ID NO: 2              moltype = DNA   length = 94
FEATURE                   Location/Qualifiers
misc_feature              1..94
                          note = synthetic sequence
misc_difference           26..45
                          note = n is a, c, g, or t
source                    1..94
                          mol_type = other DNA
                          organism = synthetic construct
SEQUENCE: 2
caacatcagt attcccaggc taaaannnn nnnnnnnnnn nnnnagatc ggaagagcgt      60
cgtgtaggga aagacctgca ggttaagcgg attg                                94

SEQ ID NO: 3              moltype = DNA   length = 42
FEATURE                   Location/Qualifiers
misc_feature              1..42
                          note = synthetic sequence
source                    1..42
                          mol_type = other DNA
                          organism = synthetic construct
SEQUENCE: 3
ttgctaggac cggccttaaa gccaatccgc ttaacctgca gg                       42

SEQ ID NO: 4              moltype = DNA   length = 42
FEATURE                   Location/Qualifiers
misc_feature              1..42
                          note = synthetic sequence
source                    1..42
                          mol_type = other DNA
                          organism = synthetic construct
SEQUENCE: 4
tagcctggga atactgatgt tgcaatccgc ttaacctgca gg                       42

SEQ ID NO: 5              moltype = DNA   length = 20
FEATURE                   Location/Qualifiers
misc_feature              1..20
                          note = synthetic sequence
source                    1..20
                          mol_type = other DNA
                          organism = synthetic construct
SEQUENCE: 5
cctgcaggtt aagcggattg                                                20

SEQ ID NO: 6              moltype = DNA   length = 52
FEATURE                   Location/Qualifiers
misc_feature              1..52
                          note = synthetic sequence
source                    1..52
                          mol_type = other DNA
                          organism = synthetic construct
SEQUENCE: 6
caagcagaag acggcatacg agatcgagta atgtgactgg agttcagacg tg            52

SEQ ID NO: 7              moltype = DNA   length = 61
FEATURE                   Location/Qualifiers
misc_feature              1..61
                          note = synthetic sequence
source                    1..61
                          mol_type = other DNA
                          organism = synthetic construct
SEQUENCE: 7
aatgatacgg cgaccaccga gatctacact atagcctaca ctctttccct acacgacgct    60
c                                                                    61

SEQ ID NO: 8              moltype = DNA   length = 90
FEATURE                   Location/Qualifiers
misc_feature              1..90
                          note = synthetic sequence
misc_difference           35..44
                          note = n is a, c, g, or t
misc_difference           60..68
                          note = n is a, c, g, or t
source                    1..90
                          mol_type = other DNA
```

-continued

```
                        organism = synthetic construct
SEQUENCE: 8
gtgactggag ttcagacgtg tgctcttccg atctnnnnnn nnnntccctt gcgatttacn    60
nnnnnnnngc tttaaggccg gtcctagcaa                                    90

SEQ ID NO: 9            moltype = DNA   length = 90
FEATURE                 Location/Qualifiers
misc_feature            1..90
                        note = synthetic sequence
misc_difference         35..44
                        note = n is a, c, g, or t
misc_difference         60..68
                        note = n is a, c, g, or t
source                  1..90
                        mol_type = other DNA
                        organism = synthetic construct
SEQUENCE: 9
gtgactggag ttcagacgtg tgctcttccg atctnnnnnn nnnntatccc ttgggatggn    60
nnnnnnnngc tttaaggccg gtcctagcaa                                    90

SEQ ID NO: 10           moltype = DNA   length = 90
FEATURE                 Location/Qualifiers
misc_feature            1..90
                        note = synthetic sequence
misc_difference         35..44
                        note = n is a, c, g, or t
misc_difference         60..68
                        note = n is a, c, g, or t
source                  1..90
                        mol_type = other DNA
                        organism = synthetic construct
SEQUENCE: 10
gtgactggag ttcagacgtg tgctcttccg atctnnnnnn nnnnctgggc aattactcgn    60
nnnnnnnngc tttaaggccg gtcctagcaa                                    90

SEQ ID NO: 11           moltype = DNA   length = 90
FEATURE                 Location/Qualifiers
misc_feature            1..90
                        note = synthetic sequence
misc_difference         35..44
                        note = n is a, c, g, or t
misc_difference         60..68
                        note = n is a, c, g, or t
source                  1..90
                        mol_type = other DNA
                        organism = synthetic construct
SEQUENCE: 11
gtgactggag ttcagacgtg tgctcttccg atctnnnnnn nnnngccgga cgacattaan    60
nnnnnnnngc tttaaggccg gtcctagcaa                                    90

SEQ ID NO: 12           moltype = DNA   length = 90
FEATURE                 Location/Qualifiers
misc_feature            1..90
                        note = synthetic sequence
misc_difference         35..44
                        note = n is a, c, g, or t
misc_difference         60..68
                        note = n is a, c, g, or t
source                  1..90
                        mol_type = other DNA
                        organism = synthetic construct
SEQUENCE: 12
gtgactggag ttcagacgtg tgctcttccg atctnnnnnn nnnnttctgg gtccctagan    60
nnnnnnnngc tttaaggccg gtcctagcaa                                    90

SEQ ID NO: 13           moltype = DNA   length = 90
FEATURE                 Location/Qualifiers
misc_feature            1..90
                        note = synthetic sequence
misc_difference         35..44
                        note = n is a, c, g, or t
misc_difference         60..68
                        note = n is a, c, g, or t
source                  1..90
                        mol_type = other DNA
                        organism = synthetic construct
SEQUENCE: 13
gtgactggag ttcagacgtg tgctcttccg atctnnnnnn nnnngtctct tggcttaaan    60
nnnnnnnngc tttaaggccg gtcctagcaa                                    90
```

```
SEQ ID NO: 14              moltype = DNA   length = 90
FEATURE                    Location/Qualifiers
misc_feature               1..90
                           note = synthetic sequence
misc_difference            35..44
                           note = n is a, c, g, or t
misc_difference            60..68
                           note = n is a, c, g, or t
source                     1..90
                           mol_type = other DNA
                           organism = synthetic construct
SEQUENCE: 14
gtgactggag ttcagacgtg tgctcttccg atctnnnnnn nnnnaatagc gagcaagtan    60
nnnnnnnngc tttaaggccg gtcctagcaa                                    90

SEQ ID NO: 15              moltype = DNA   length = 90
FEATURE                    Location/Qualifiers
misc_feature               1..90
                           note = synthetic sequence
misc_difference            35..44
                           note = n is a, c, g, or t
misc_difference            60..68
                           note = n is a, c, g, or t
source                     1..90
                           mol_type = other DNA
                           organism = synthetic construct
SEQUENCE: 15
gtgactggag ttcagacgtg tgctcttccg atctnnnnnn nnnngctgcg ctttccattn    60
nnnnnnnngc tttaaggccg gtcctagcaa                                    90

SEQ ID NO: 16              moltype = DNA   length = 90
FEATURE                    Location/Qualifiers
misc_feature               1..90
                           note = synthetic sequence
misc_difference            35..44
                           note = n is a, c, g, or t
misc_difference            60..68
                           note = n is a, c, g, or t
source                     1..90
                           mol_type = other DNA
                           organism = synthetic construct
SEQUENCE: 16
gtgactggag ttcagacgtg tgctcttccg atctnnnnnn nnnncaatca gacctatgan    60
nnnnnnnngc tttaaggccg gtcctagcaa                                    90

SEQ ID NO: 17              moltype = DNA   length = 90
FEATURE                    Location/Qualifiers
misc_feature               1..90
                           note = synthetic sequence
misc_difference            35..44
                           note = n is a, c, g, or t
misc_difference            60..68
                           note = n is a, c, g, or t
source                     1..90
                           mol_type = other DNA
                           organism = synthetic construct
SEQUENCE: 17
gtgactggag ttcagacgtg tgctcttccg atctnnnnnn nnnnatatgt atcacgcgan    60
nnnnnnnngc tttaaggccg gtcctagcaa                                    90

SEQ ID NO: 18              moltype = DNA   length = 90
FEATURE                    Location/Qualifiers
misc_feature               1..90
                           note = synthetic sequence
misc_difference            35..44
                           note = n is a, c, g, or t
misc_difference            60..68
                           note = n is a, c, g, or t
source                     1..90
                           mol_type = other DNA
                           organism = synthetic construct
SEQUENCE: 18
gtgactggag ttcagacgtg tgctcttccg atctnnnnnn nnnntcaatc cttccgcttn    60
nnnnnnnngc tttaaggccg gtcctagcaa                                    90

SEQ ID NO: 19              moltype = DNA   length = 90
FEATURE                    Location/Qualifiers
misc_feature               1..90
```

```
                         note = synthetic sequence
misc_difference          35..44
                         note = n is a, c, g, or t
misc_difference          60..68
                         note = n is a, c, g, or t
source                   1..90
                         mol_type = other DNA
                         organism = synthetic construct
SEQUENCE: 19
gtgactggag ttcagacgtg tgctcttccg atctnnnnnn nnnnctccga atcatgttgn    60
nnnnnnnngc tttaaggccg gtcctagcaa                                    90

SEQ ID NO: 20            moltype = DNA   length = 90
FEATURE                  Location/Qualifiers
misc_feature             1..90
                         note = synthetic sequence
misc_difference          35..44
                         note = n is a, c, g, or t
misc_difference          60..68
                         note = n is a, c, g, or t
source                   1..90
                         mol_type = other DNA
                         organism = synthetic construct
SEQUENCE: 20
gtgactggag ttcagacgtg tgctcttccg atctnnnnnn nnnngtccct gcaacttgan    60
nnnnnnnngc tttaaggccg gtcctagcaa                                    90

SEQ ID NO: 21            moltype = DNA   length = 90
FEATURE                  Location/Qualifiers
misc_feature             1..90
                         note = synthetic sequence
misc_difference          35..44
                         note = n is a, c, g, or t
misc_difference          60..68
                         note = n is a, c, g, or t
source                   1..90
                         mol_type = other DNA
                         organism = synthetic construct
SEQUENCE: 21
gtgactggag ttcagacgtg tgctcttccg atctnnnnnn nnnntccac ttccgctttn     60
nnnnnnnngc tttaaggccg gtcctagcaa                                    90

SEQ ID NO: 22            moltype = DNA   length = 90
FEATURE                  Location/Qualifiers
misc_feature             1..90
                         note = synthetic sequence
misc_difference          35..44
                         note = n is a, c, g, or t
misc_difference          60..68
                         note = n is a, c, g, or t
source                   1..90
                         mol_type = other DNA
                         organism = synthetic construct
SEQUENCE: 22
gtgactggag ttcagacgtg tgctcttccg atctnnnnnn nnnntggatt cccggacttn    60
nnnnnnnngc tttaaggccg gtcctagcaa                                    90

SEQ ID NO: 23            moltype = DNA   length = 90
FEATURE                  Location/Qualifiers
misc_feature             1..90
                         note = synthetic sequence
misc_difference          35..44
                         note = n is a, c, g, or t
misc_difference          60..68
                         note = n is a, c, g, or t
source                   1..90
                         mol_type = other DNA
                         organism = synthetic construct
SEQUENCE: 23
gtgactggag ttcagacgtg tgctcttccg atctnnnnnn nnnncgcgaa cataagaagn    60
nnnnnnnngc tttaaggccg gtcctagcaa                                    90

SEQ ID NO: 24            moltype = DNA   length = 90
FEATURE                  Location/Qualifiers
misc_feature             1..90
                         note = synthetic sequence
misc_difference          35..44
                         note = n is a, c, g, or t
misc_difference          60..68
```

```
                        note = n is a, c, g, or t
source                  1..90
                        mol_type = other DNA
                        organism = synthetic construct
SEQUENCE: 24
gtgactggag ttcagacgtg tgctcttccg atctnnnnnn nnnncagtcg tggtagatan    60
nnnnnnnngc tttaaggccg gtcctagcaa                                    90

SEQ ID NO: 25           moltype = DNA  length = 90
FEATURE                 Location/Qualifiers
misc_feature            1..90
                        note = synthetic sequence
misc_difference         35..44
                        note = n is a, c, g, or t
misc_difference         60..68
                        note = n is a, c, g, or t
source                  1..90
                        mol_type = other DNA
                        organism = synthetic construct
SEQUENCE: 25
gtgactggag ttcagacgtg tgctcttccg atctnnnnnn nnnnatatgt cagagcaccn    60
nnnnnnnngc tttaaggccg gtcctagcaa                                    90

SEQ ID NO: 26           moltype = DNA  length = 90
FEATURE                 Location/Qualifiers
misc_feature            1..90
                        note = synthetic sequence
misc_difference         35..44
                        note = n is a, c, g, or t
misc_difference         60..68
                        note = n is a, c, g, or t
source                  1..90
                        mol_type = other DNA
                        organism = synthetic construct
SEQUENCE: 26
gtgactggag ttcagacgtg tgctcttccg atctnnnnnn nnnnggtggc tagataatgn    60
nnnnnnnngc tttaaggccg gtcctagcaa                                    90

SEQ ID NO: 27           moltype = DNA  length = 90
FEATURE                 Location/Qualifiers
misc_feature            1..90
                        note = synthetic sequence
misc_difference         35..44
                        note = n is a, c, g, or t
misc_difference         60..68
                        note = n is a, c, g, or t
source                  1..90
                        mol_type = other DNA
                        organism = synthetic construct
SEQUENCE: 27
gtgactggag ttcagacgtg tgctcttccg atctnnnnnn nnnngagatg tctgcaactn    60
nnnnnnnngc tttaaggccg gtcctagcaa                                    90
```